United States Patent
Brendel et al.

(10) Patent No.: US 6,529,103 B1
(45) Date of Patent: Mar. 4, 2003

(54) INTERNALLY GROUNDED FEEDTHROUGH FILTER CAPACITOR WITH IMPROVED GROUND PLANE DESIGN FOR HUMAN IMPLANT AND OTHER APPLICATIONS

(75) Inventors: Richard L. Brendel, Carson City, NV (US); Robert A. Stevenson, Canyon Country, CA (US)

(73) Assignee: Greatbatch-Sierra, Inc., Clarence, NY (US)

( * ) Notice: Subject to any disclaimer, the term of this patent is extended or adjusted under 35 U.S.C. 154(b) by 0 days.

(21) Appl. No.: 09/657,123

(22) Filed: Sep. 7, 2000

(51) Int. Cl.$^7$ ................................................. H03H 7/01
(52) U.S. Cl. ..................... 333/182; 333/185; 361/302
(58) Field of Search ............................... 333/182, 185; 361/302

(56) References Cited

U.S. PATENT DOCUMENTS

| | | | |
|---|---|---|---|
| 2,756,375 A | 7/1956 | Peck | 361/302 |
| 3,235,939 A | 2/1966 | Rodriguez et al. | 361/302 |
| 3,538,464 A | 11/1970 | Walsh | 361/302 |
| 3,548,347 A * | 12/1970 | Miller et al. | 333/182 |
| 3,920,888 A | 11/1975 | Barr | 361/302 |
| 4,083,022 A | 4/1978 | Nijman | 361/302 |
| 4,144,509 A | 3/1979 | Boutros | 361/302 |
| 4,148,003 A | 4/1979 | Colburn et al. | 361/302 |
| 4,152,540 A | 5/1979 | Duncan et al. | 361/302 |
| 4,220,813 A | 9/1980 | Kyle | 361/302 |
| 4,247,881 A | 1/1981 | Coleman | 361/302 |
| 4,314,213 A | 2/1982 | Wakino | 361/302 |
| 4,352,951 A | 10/1982 | Kyle | 361/302 |
| 4,362,792 A | 12/1982 | Bowsky et al. | 361/302 |
| 4,424,551 A | 1/1984 | Stevenson et al. | 361/302 |
| 5,333,095 A | 7/1994 | Stevenson et al. | 361/302 |
| 5,650,759 A * | 7/1997 | Hittman et al. | 333/182 |
| 5,751,539 A | 5/1998 | Stevenson et al. | 361/302 |
| 5,817,130 A * | 10/1998 | Cox et al. | 607/5 |
| 5,905,627 A | 5/1999 | Brendel et al. | 361/302 |
| 5,973,906 A | 10/1999 | Stevenson et al. | 361/302 |
| 6,008,980 A | 12/1999 | Stevenson et al. | 361/302 |

\* cited by examiner

*Primary Examiner*—Justin P. Bettendorf
(74) *Attorney, Agent, or Firm*—Kelly Bauersfeld Lowry & Kelley, LLP

(57) ABSTRACT

An improved internally grounded feedthrough filter capacitor includes at least one conductive terminal pin, a feedthrough filter capacitor having first and second sets of electrode plates and a first passageway through which the terminal pin extends in conductive relation with the first set of electrode plates, and a conductive ferrule through which the terminal pin passes in non-conductive relation. A conductive ground plane includes a plate which substantially spans and supports an adjacent face of the feedthrough filter capacitor, and an integral grounded terminal pin which extends into a second passageway through the feedthrough filter capacitor in conductive relation with the second set of electrode plates. A washer electrically insulates the feedthrough filter capacitor from the conductive ferrule except for the conductive relation between the grounded terminal pin and the second set of electrode plates.

56 Claims, 13 Drawing Sheets

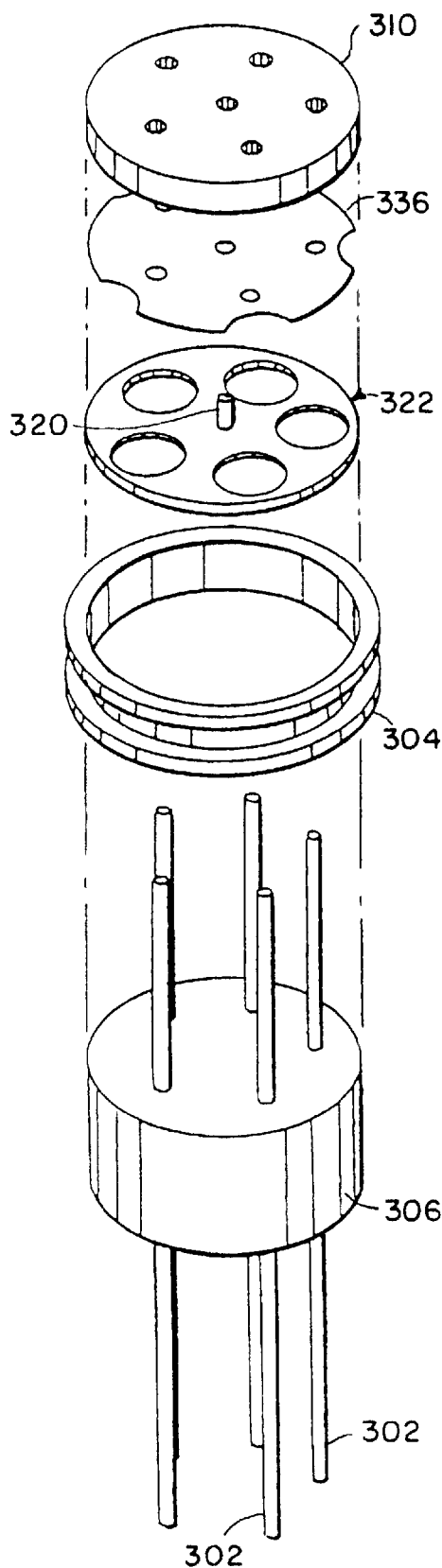
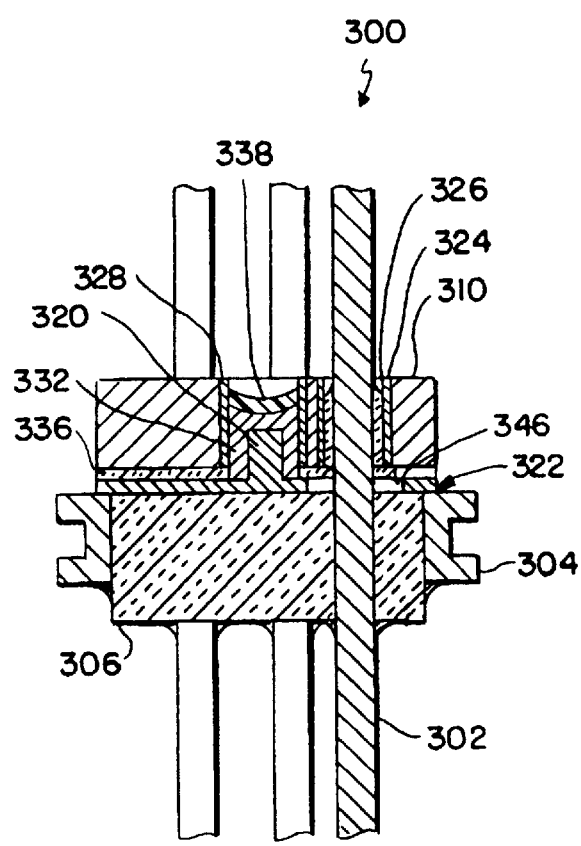
FIG. 14
FIG. 15

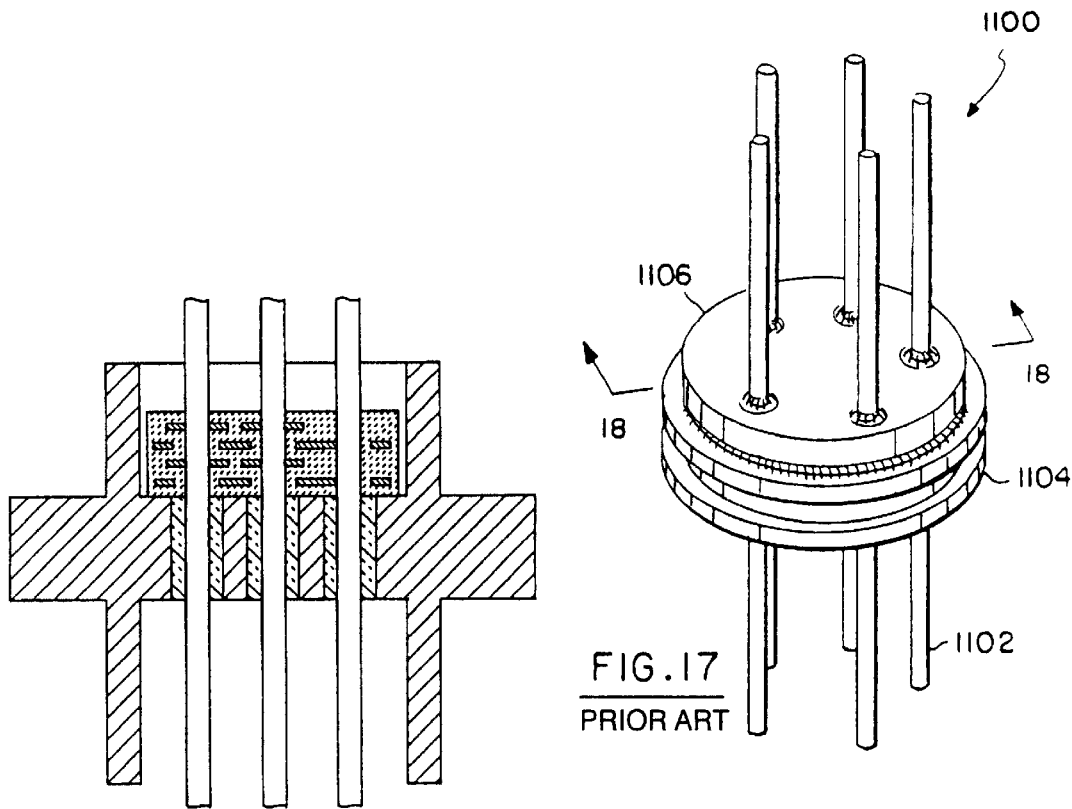
FIG. 16
PRIOR ART
FIG. 17
PRIOR ART
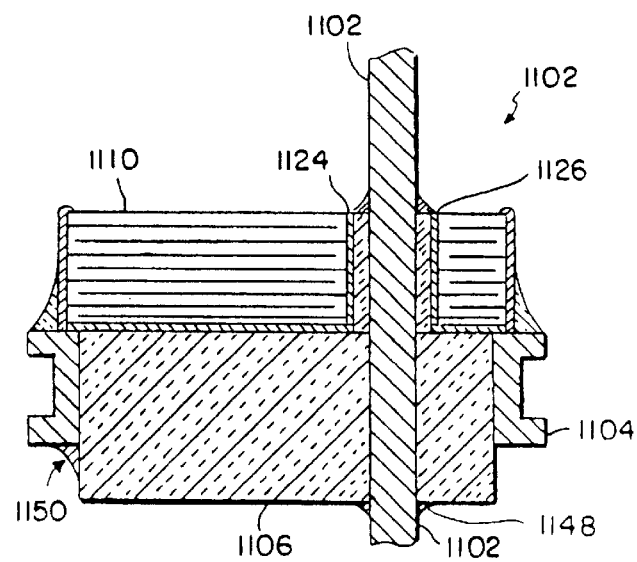
FIG. 18
PRIOR ART

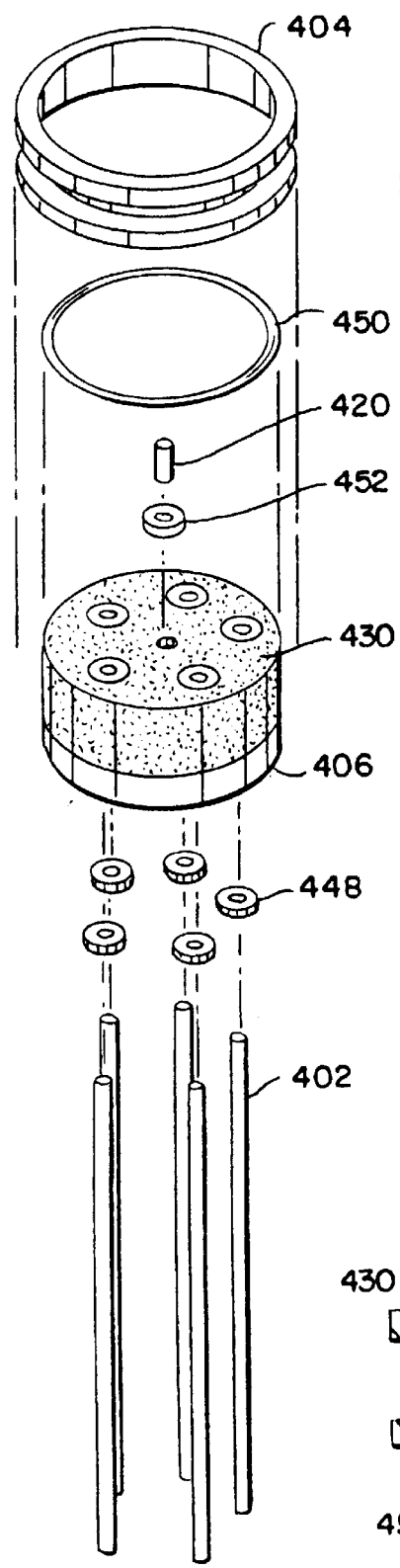
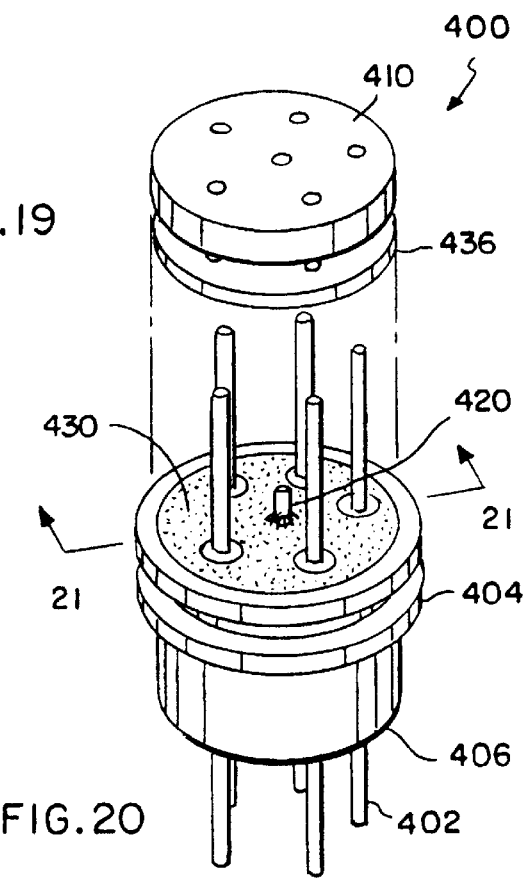
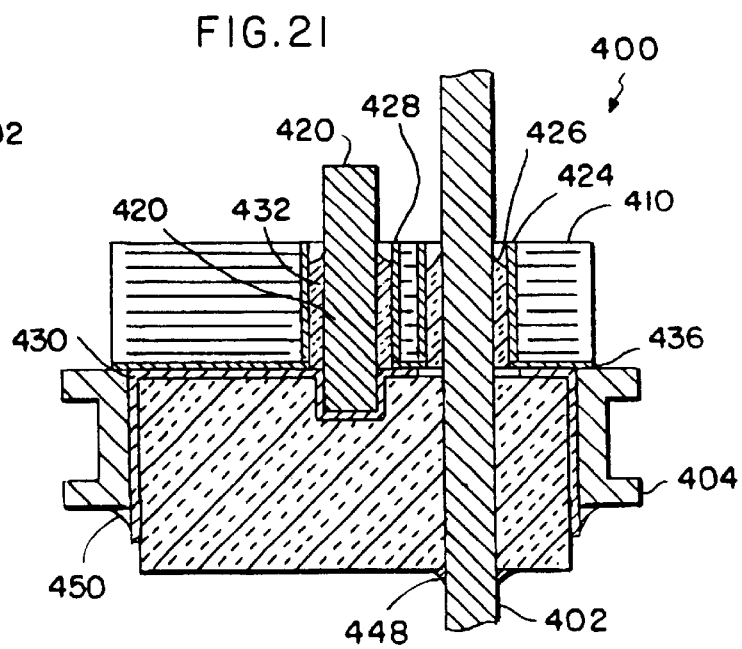
FIG.19
FIG.20
FIG.21

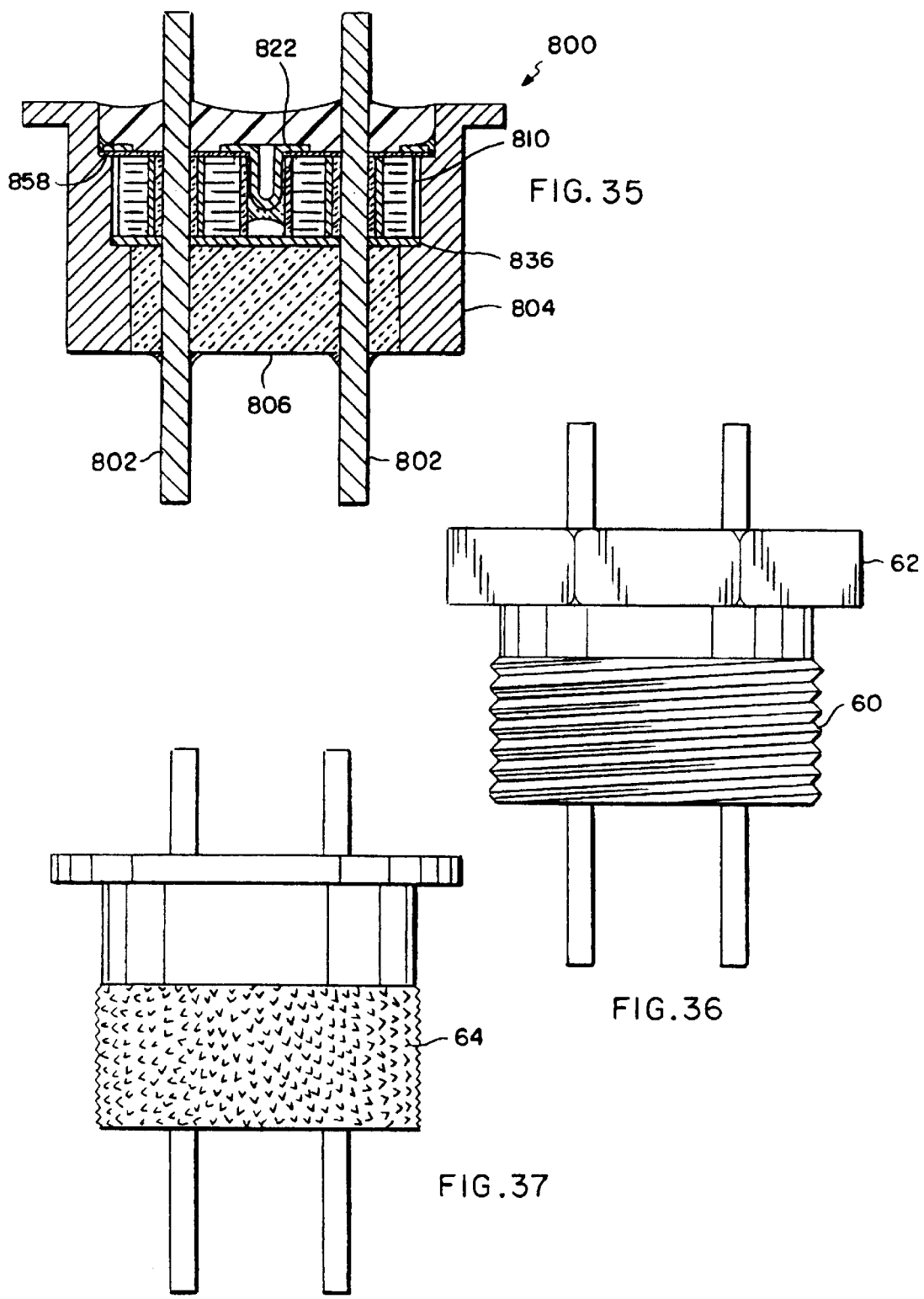

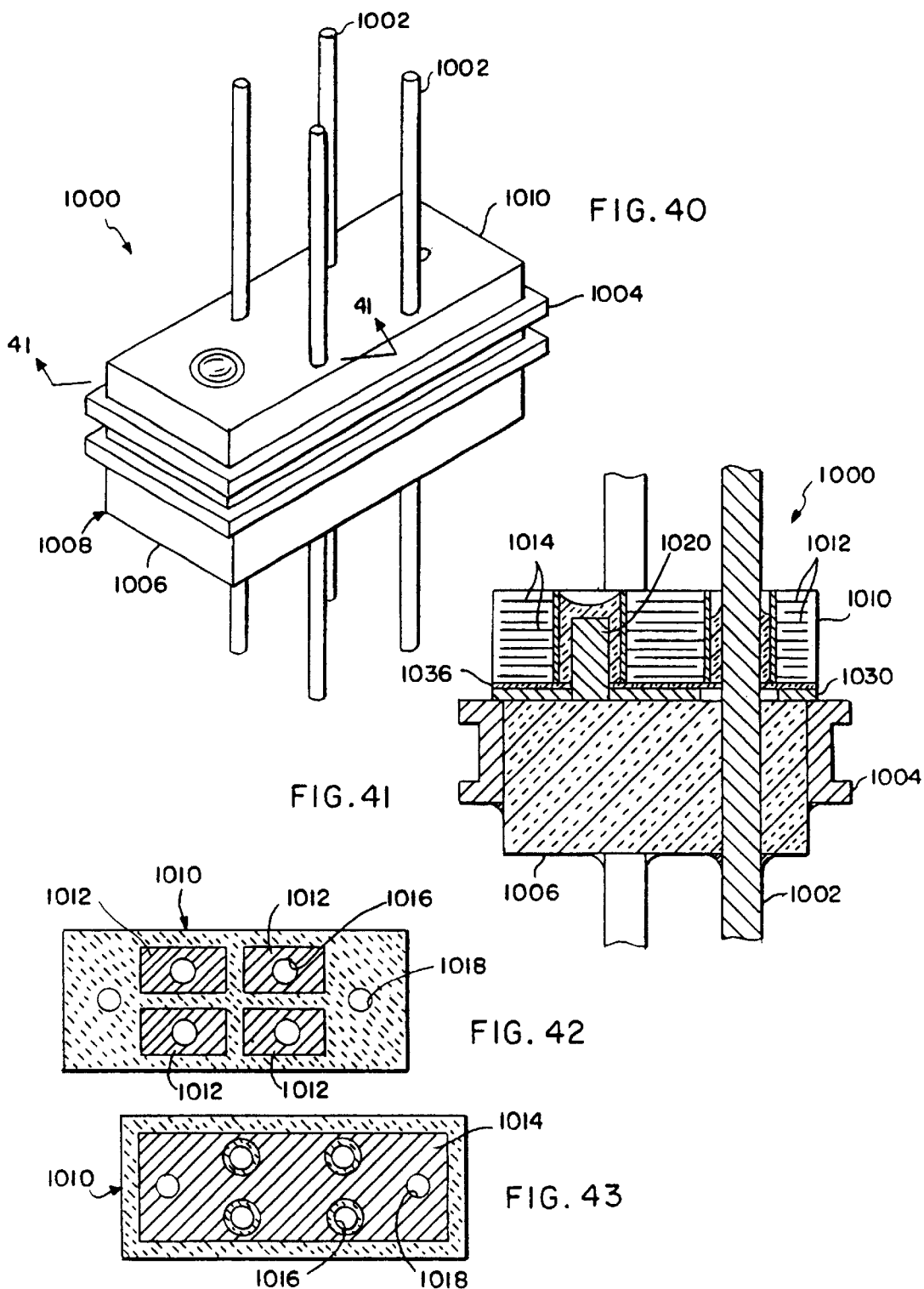

INTERNALLY GROUNDED FEEDTHROUGH FILTER CAPACITOR WITH IMPROVED GROUND PLANE DESIGN FOR HUMAN IMPLANT AND OTHER APPLICATIONS

BACKGROUND OF THE INVENTION

This invention relates generally to an improved ground plane design of simplified feedthrough terminal pin subassemblies and related methods of construction, particularly of the type used in implantable medical devices such as cardiac pacemakers and the like, to decouple and shield undesirable electromagnetic interference (EMI) signals from the device. More specifically, this invention relates to a reduced cost and reduced mechanical stress hermetic feedthrough terminal pin and ceramic feedthrough capacitor assembly including one or more filter capacitors, and related installation method. It is adapted particularly for use in connecting a lead wire or electrode through a hermetically sealed housing to internal electronic components of the medical device while decoupling EMI against entry into the sealed housing. This invention is specifically designed for use in cardiac pacemakers (bradycardia devices), cardioverter defibrillators (tachycardia devices) and combined pacemaker defibrillator devices. This invention is also applicable to a wide range of other EMI filter applications, such as military or space electronic modules where it is desirable to preclude the entry of EMI into a sealed housing containing sensitive electronic circuitry.

Feedthrough terminal pin assemblies are generally well known in the art for connecting electrical signals through the housing or case of an electronic instrument. For example, in implantable medical devices such as cardiac pacemakers, defibrillators or the like, the terminal pin assembly comprises one or more conductive terminal pins supported by an insulator structure for feedthrough passage from the exterior to the interior of the medical device. Many different insulator structures and related mounting methods are known in the art for use in medical devices wherein the insulator structure also provides a hermetic seal to prevent entry of body fluids into the housing of the medical device. Said hermetic insulators for medical implant applications are typically constructed of alumina ceramic or glass wherein the terminal pins and ferrule are of suitable biocompatible material such as platinum, platinum-iridium, niobium, or tantalum and titanium respectively. However, the feedthrough terminal pins are typically connected to one or more exterior lead wires, for example, the leads which connect a cardiac pacemaker to the ventricle chamber of the heart, which also effectively act as an antenna and thus tend to collect stray EMI signals for transmission into the interior of the medical device. In many prior art devices, the hermetic terminal pin assembly has been combined directly with a ceramic feedthrough filter capacitor to decouple interference signals to the housing of the medical device. A major market force within the medical implantable device industry has been to reduce cost of the implanted device (e.g. pacemaker or implantable cardioverter defibrillator). Medical insurance carriers, government healthcare programs (e.g. Medicare) and health maintenance organizations (HMOs) are placing additional competitive pressures on the manufacturers of such devices.

In a typical unipolar construction, as described in U.S. Pat. No. 5,333,095 (the contents of which are incorporated herein), a coaxial ceramic feedthrough filter capacitor used in a feedthrough assembly to suppress and decouple undesired interference or noise transmission along a terminal pin comprises a so-called discoidal capacitor having two sets of electrode plates embedded in spaced relation within an insulative dielectric substrate or base, formed typically as a ceramic monolithic structure. One set of the electrode plates is electrically connected at an inner diameter cylindrical surface of the discoidal capacitor structure to the conductive terminal pin utilized to pass the desired electrical signal or signals. The other or second set of electrode plates is coupled at an outer diameter surface of the discoidal capacitor to a cylindrical ferrule of conductive material, wherein the ferrule is electrically connected in turn to the conductive housing of the electronic device. The number and dielectric thickness spacing of the electrode plate sets varies in accordance with the capacitance value and the voltage rating of the discoidal capacitor. In operation, the discoidal capacitor permits passage of relatively low frequency electrical signals along the terminal pin, while shielding and decoupling/attenuating undesired interference signals of typically high frequency to the conductive housing. Feedthrough capacitors of this general type are available in unipolar (one), bipolar (two), tripolar (three), quadpolar (four), pentapolar (five), hexpolar (six) and additional lead configurations. The feedthrough capacitors of this general type are commonly employed in implantable cardiac pacemakers and defibrillators and the like, wherein the pacemaker housing is constructed from a biocompatible metal, such as titanium alloy, which is electrically coupled to the feedthrough filter capacitor. As a result, the filter capacitor and terminal pin assembly prevents entrance of interference signals to the interior of the pacemaker housing, wherein such interference signals could otherwise adversely affect the desired cardiac pacing or defibrillation function.

In the past, feedthrough filter capacitors for cardiac pacemakers and the like have typically been constructed by preassembly of the discoidal capacitor within a cylindrical terminal pin subassembly which includes the conductive pin and ferrule. More specifically, the terminal pin subassembly is prefabricated to include one or more conductive terminal pins supported within the conductive ferrule by means of a hermetically sealed insulator ring or bead. See, for example, the subassemblies disclosed in U.S. Pat. Nos. 3,920,888; 4,152,540; 4,421,947; and 4,424,551. An improved design which has substantially improved the volumetric efficiency is based upon surface mounting of a ceramic feedthrough capacitor planar array structure to one outer surface of a hermetic terminal with similar connection to the conductive pins (see the subassemblies disclosed in U.S. Pat. No. 5,333,095). In all of the prior art described above, the outer feedthrough capacitor electrode plate sets are coupled in parallel together by a metallized layer which is either fired, sputtered or plated onto the ceramic capacitor. This metallized band, in turn, is coupled to the ferrule by conductive adhesive, soldering, brazing, or the like.

Although feedthrough filter capacitor assemblies of the type described above have performed in a generally satisfactory manner, the manufacture and installation of such filter capacitor assemblies has been relatively time consuming and therefore costly. For example, installation of the discoidal capacitor into the small annular space described by U.S. Pat. No. 4,424,551 between the terminal pin and ferrule can be a difficult and complex multi-step procedure to ensure formation of reliable, high quality electrical connections. The method taught by U.S. Pat. No. 4,424,551 (the contents of which are incorporated herein), teaches the injection of fluidic thermosetting conductive particles into first and second annular cavities (usually by centrifuge operations). As a consequence, this method also requires insulation of the interface between the capacitor structure and insulator, curing of the various thermosetting materials, and subsequent cleaning operations to remove excess conductive material. While the method taught by U.S. Pat. No. 5,333,095 is far simpler, a connection from the capacitor outside diameter and the conductive ferrule is still required.

A high integrity hermetic seal for medical implant applications is very critical to prevent the ingress of body fluids into the implanted device (e.g. pacemaker). Even a small leak rate of such body fluid penetration can, over a period of many years, build up and damage sensitive internal electronic components. This can cause catastrophic failure of the implanted device. The hermetic seal for medical implant (as well as space and military) applications is typically constructed of highly stable alumina ceramic or glass materials with very low bulk permeability. A helium fine leak test is typically used in conjunction with a sensitive detector to reject defective or cracked hermetic seals. This final product quality conformance test is typically of very short duration (a few seconds helium exposure). This short test exposure will readily detect a leak in a cracked or otherwise defective alumina ceramic or glass hermetic seal; however, it typically takes much longer for helium to penetrate through an epoxy or polymide adjunct barrier (such polymer overcoating can mask the leak).

Withstanding the high temperature and thermal stresses associated with the welding of a hermetically sealed terminal with a premounted ceramic feedthrough capacitor is very difficult to achieve with the '551, '095 and other prior art designs. The electrical/mechanical connection to the outside perimeter or outside diameter of the feedthrough capacitor has a very high thermal conductivity as compared to air. The hermetic bonding operation typically employed in the medical implant industry to install the filtered hermetic terminal into the implantable device housing typically involves a laser welding operation in very close proximity to this electrical/mechanical connection area. Accordingly, in the prior art, the ceramic feedthrough capacitor is subjected to a dramatic temperature rise. This temperature rise produces mechanical stress in the capacitor due to the mismatch in thermal coefficients of expansion of the surrounding materials. In addition, the capacitor lead connections in the prior art must be of very high temperature materials to withstand the high peak temperatures reached during the welding operation (as much as 500° C.). A similar situation is applicable in military, space and commercial applications where similar prior art devices are soldered instead of welded by the user into a bulkhead or substrate. Many of these prior art devices employ a soldered connection to the outside perimeter or outside diameter of the feedthrough capacitor. Excessive installation soldering heat has been known to damage such devices.

Accordingly, there is a need for a novel feedthrough filter capacitor assembly that addresses the drawbacks noted above in connection with the prior art. In particular, a novel capacitor assembly is needed that is subjected to far less temperature rise during the manufacture thereof by eliminating an outside perimeter or outside diameter electrical/mechanical connection. Such a design would allow the use of much lower temperature materials (such as standard solder) to achieve the capacitor inside diameter lead connections. Moreover, such an improvement would make the assembly relatively immune to the aforementioned stressful installation techniques. A novel filter capacitor design is needed which is of simplified construction, utilizing a straightforward and uncomplicated feedthrough terminal pin subassembly that can result in manufacturing cost reductions. Of course the new design must be capable of effectively filtering out undesirable electromagnetic interference (EMI) signals from the target device. The present invention fulfills these needs and provides other related advantages.

SUMMARY OF THE INVENTION

The present invention resides in improved ground plane designs for an internally grounded ceramic feedthrough filter capacitor assembly for shielding and decoupling of a conductive terminal pin or lead of the type used, for example, in an implantable medical device such as a cardiac pacemaker, cardioverter defibrillator, cochlear implant, neurostimulator or the like to prevent the passage of externally generated electromagnetic (EM) fields such as interference signals caused by digital cellular telephones. The feedthrough filter capacitor assembly is typically mounted upon a conductive substrate such as, for example, a conductive pacemaker housing. The assembly comprises, generally, at least one conductive terminal pin and means for mounting the terminal pin for passage through an opening formed in the conductive substrate with the terminal pin and the substrate in non-conductive relation. A feedthrough filter capacitor is provided which has first and second sets of electrode plates. The terminal pin extends through a first passageway through the feedthrough filter capacitor in conductive relation with the first set of electrode plates. A ground lead extends into a second passageway through the feedthrough filter capacitor and is conductively coupled to the second set of electrode plates and the conductive substrate.

The terminal pin mounting means comprises a conductive ferrule adapted for mounting onto the substrate in a position extending through the substrate opening, and insulator means for supporting the terminal pin from the ferrule in electrically insulated relation. The terminal pin, ferrule and insulator means comprise a prefabricated terminal pin subassembly.

Various embodiments of the invention with an improved ground plane design are disclosed herein which illustrate (1) that the feedthrough filter capacitor may be asymmetrical as well as symmetrical about the ground lead, (2) that the ground plane and grounded terminal pin may be machined in one piece as an integral part of the machined ferrule of the hermetic insulator, (3) that the terminal pin may be added by welding or brazing to an machined ground plane which is an integral part of said ferrule, (4) that the ground plane and grounded terminal be co-formed by metal stamping of a ground plate which is subsequently attached to the ferrule by welding, brazing, bonding or the like, (5) that the ground plane be constructed of thin metallic material which is chemically etched to the proper shape which is subsequently attached to the ferrule by welding, brazing, bonding or the like with a ground terminal pin subsequently added by any of the aforementioned means, or (6) that the ground plane be deposited by sputtered or equivalent metal deposition process to the insulator surface with a ground terminal pin subsequently added by any of the above aforementioned means. The sputtered surface may optionally have additional metal added to increase its thickness and thereby increase its effectiveness as an EMI shield and low impedance ground plane. For example, additional thickness may be achieved by plating on a metallic coating of various conductive materials such as nickel, gold or the like.

As described in U.S. Pat. No. 5,905,627 (the contents of which are incorporated herein), any of the improved ground plane designs may include a wire bond pad at one end thereof, and the ground lead may comprise a solid pin or a hollow gas back-fill tubelet, etc. The ground lead may comprise a nail-head lead having one end that abuts a portion of the conductive ferrule and, if desired, the nail head lead may extend from the conductive ferrule through and beyond the feedthrough filter capacitor to provide a ground pin. Alternatively, the ground lead may comprise a ground pin that extends through the conductive ferrule and feedthrough filter capacitor. In this case, means may be provided for hermetically sealing passage of the terminal pin and the ground pin through the conductive substrate. A desirable feature of the improved ground plane design as described herein is that it may be easily added to an existing hermetic seal terminal so that said hermetic seal is thereby retrofitted to accept the internally grounded feedthrough capacitor. Also described is a method to form a hermetic seal and ground pin directly to the titanium housing or subplate of an implantable medical device or the like thereby eliminating the need for a separate and expensive ferrule and the subsequent installation process wherein said ferrule is hermetically and conductively attached to said housing, for example, by laser welding.

Utilization of an internally grounded feedthrough filter capacitor as disclosed herein permits use of a capacitor having non-metallized (insulative) exterior surfaces. This is of particular importance in miniature high voltage feedthrough capacitor devices of the type, for example, used in implantable defibrillators wherein the gap distance between each high voltage terminal pin and ground must be as large as possible to prevent HV breakdown or flashover across the capacitor surface. Elimination of the metallized ground band around the outside diameter or perimeter of the feedthrough capacitor effectively increases the HV flashover distance by the height of the capacitor itself. A ferrite bead disc inductor may also be utilized in connection with the feedthrough filter capacitor to enhance the filtering performance and characteristics of the capacitor assembly.

In one preferred form of the invention for medical implant applications, the feedthrough filter capacitor assembly includes a terminal pin subassembly having at least one terminal pin supported within a conductive ferrule by a hermetically sealed insulator structure. The ferrule is adapted for mounting into a conductive pacemaker housing by welding or brazing to support the terminal pin subassembly for feedthrough passage to the interior of the housing. A ceramic feedthrough capacitor is mounted at either an inboard side or on the body fluid side of the terminal pin subassembly, with capacitor electrode plate sets coupled respectively to a ground pin and to active terminal pin(s) by conductive adhesive, soldering, brazing or the like. As shown, multiple feedthrough filter capacitors are provided in a substantially coplanar array within a common base structure, with each capacitor in association with a respective terminal pin.

The internally grounded monolithic feedthrough filter capacitors utilized in the assemblies of the present invention advantageously eliminate the need to conductively couple a metallized exterior surface of the capacitor to a portion of the conductive substrate or ferrule, as was required in the prior art.

An important feature of the improved ground plane design(s) as described herein is that it acts as a continuous part of the overall electromagnetic shield or housing of the electronic device to be protected. Accordingly, the improved ground plane with its grounded terminal pin is designed to present a low impedance path between the ground plane electrode set of the feedthrough capacitor EMI filter and said electromagnetic shield/housing. The improved ground plate designs presented herein are particularly efficient in presenting a low impedance path by minimizing the inductive and resistive components in the conductive path between said ground plane electrode set and the electromagnetic shield housing. More particularly, the radial shape of the improved ground plane acts to reduce inductance between the electromagnetic shield housing (or ferrule of the insulator terminal) and the grounded terminal pin which connects to the feedthrough capacitor ground plane electrode set. Resistive components are minimized by the use of high quality electrical connections such as co-machining, welding, brazing, conductive thermosetting polymers, solder or the like between the electromagnetic shield/housing and the ferrule, the ferrule and the ground plane, the ground plane and the grounded terminal pin and between the grounded terminal pin and the feedthrough capacitor ground plane electrode plate set.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 14 is an exploded perspective view of a feedthrough capacitor hermetic terminal pin assembly similar to that shown in FIG. 5, wherein the outer diameter of an insulator washer has been notched-out in five places to provide a hermetic seal test leak path for helium detection gas or the like;

FIG. 15 is an enlarged, partially fragmented sectional view through the assembled feedthrough capacitor assembly of FIG. 14;

FIG. 16 is an exploded perspective assembly view of a prior art quadpolar hermetic feedthrough capacitor terminal;

FIG. 17 is a top and side perspective view of the prior art quadpolar hermetic seal terminal of FIG. 16 after the various components have been assembled to one another;

FIG. 18 is an enlarged, partially fragmented sectional view taken generally along the line 18—18 of FIG. 17;

FIG. 19 is an exploded perspective assembly view of a pentapolar hermetic terminal with a metal deposit ground plane formed by sputtering, plating, arc deposition or the like, and a counter-bored hole to receive a ground pin which is prepared for subsequent installation of an internally grounded feedthrough capacitor;

FIG. 20 is a top and side perspective view of the pentapolar terminal assembly with a sputtered ground plane of FIG. 19, prepared to accept installation of the internally grounded feedthrough capacitor, (shown exploded from the terminal pin subassembly);

FIG. 21 is an enlarged, partially fragmented sectional view taken generally along the line 21—21 of FIG. 20, illustrating the internally grounded feedthrough capacitor as assembled to the underlying terminal pin subassembly;

FIG. 31 is a sectional view of another form of bipolar feedthrough capacitor assembly similar to FIG. 27, including an inductor and a stamped ground plane designed to fit the inside diameter of a ferrule and to be electrically and mechanically attached by press-in fit, soldering, welding, brazing, co-machining conductive polymer or the like;

FIG. 35 is a cross-sectional view of another feedthrough capacitor similar to FIGS. 27 and 31, illustrating a ground plane washer for an isolated ground feedthrough filter capacitor which is inverted and fitted into a ferrule having a step or counter-bore to seat/locate the ground plane washer;

FIG. 36 is an elevational view of an exemplary bipolar or quadpolar internally grounded EMI filter similar to those shown in FIGS. 27, 31 and 35, illustrating optional mounting threads and a hex head for convenient screw-in installation into a threaded aperture or into a bulk head with a nut and lock washer;

FIG. 37 is a side elevational view similar to that shown in FIG. 36, illustrating an optional knurled surface for installation by pressing into a mating aperture in a bulk head or plate;

FIG. 40 is a perspective view of a rectangular monolithic ceramic, internally grounded quadpolar feedthrough filter capacitor including dual ground pins;

FIG. 41 is an enlarged, partially fragmented sectional view taken generally along the line 41—41 of FIG. 40;

FIG. 42 illustrates the electrode lay-up pattern for the four active sets of electrodes for the quadpolar feedthrough capacitor of FIGS. 40 and 41; and FIG. 43 illustrates the lay-up pattern for the set of ground electrodes for the quadpolar feedthrough capacitor of FIGS. 40 and 41.

DETAILED DESCRIPTION OF THE PREFERRED EMBODIMENTS

Figure 8:
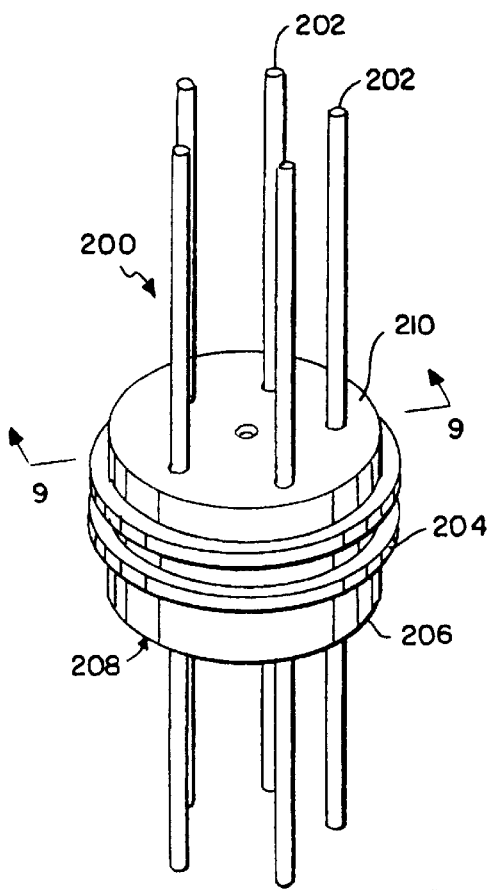
FIG. 8 is a perspective view of a monolithic, ceramic internally grounded bypolar feedthrough filter capacitor assembly similar to that illustrated in FIG. 1, incorporating the alternative ground plane of FIGS. 6 and 7.
Figure 9:
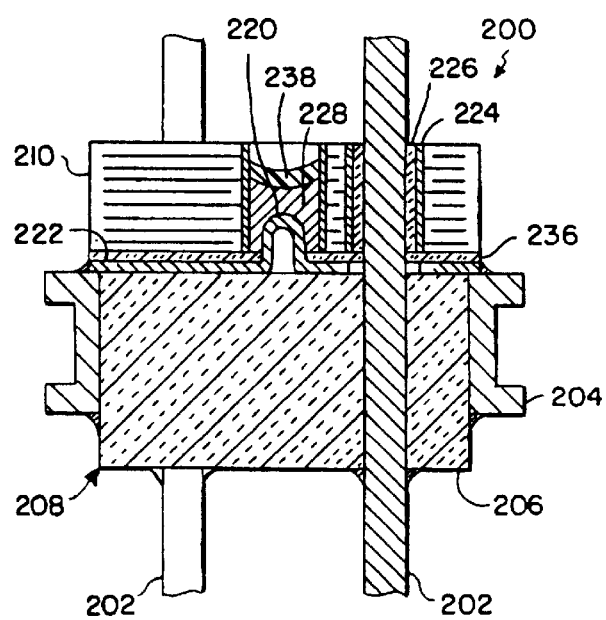
FIG. 9 is an enlarged, partially fragmented sectional view taken generally along the line 9—9 of FIG. 8.
Figure 22:
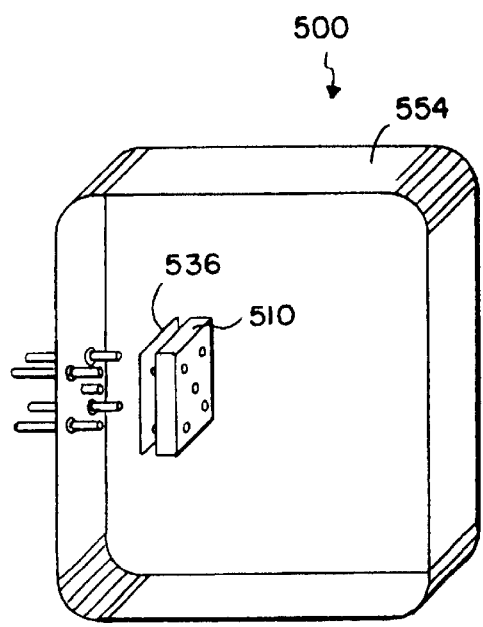
FIG. 22 is a perspective view of the housing for a quadpolar cardiac pacemaker or similar medical device wherein the hermetic seal to each terminal pin is formed directly to the housing, and further illustrating an insulator and an internally grounded quadpolar feedthrough capacitor in exploded relation relative to the terminal pins.
Figure 23:
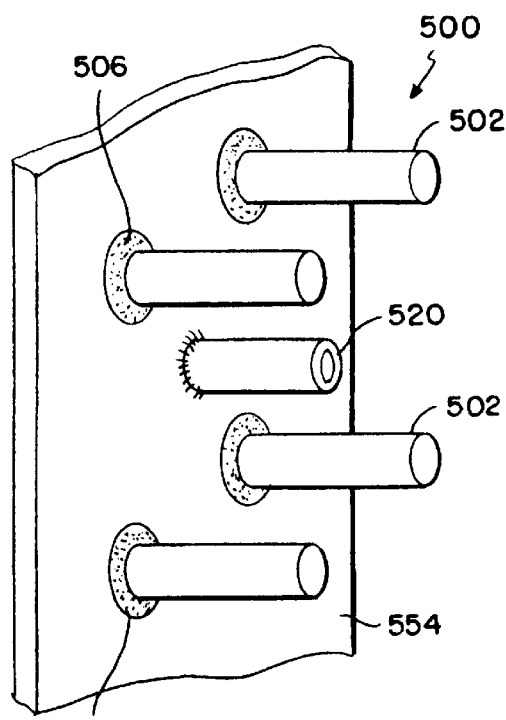
FIG. 23 is an enlarged perspective view of the housing of FIG. 22, illustrating use of an optional hollow gas fill tubelet provided for convenient vacuum evacuation of the implantable medical device and subsequent back-fill with an inert gas.
Figure 26:
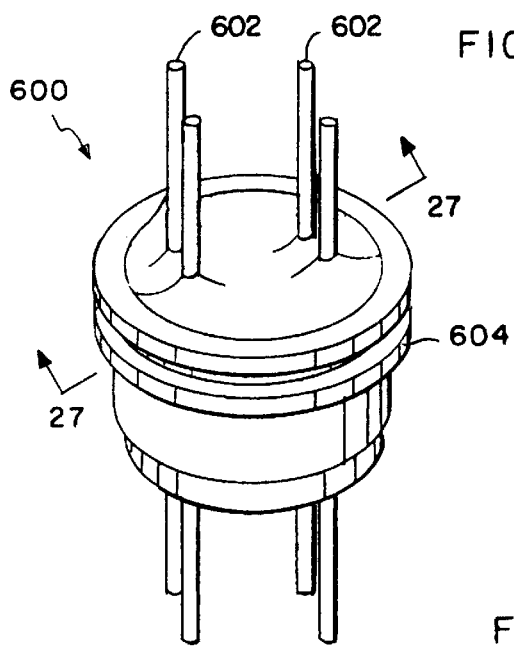
FIG. 26 is a top and side perspective view of a quadpolar isolated ground feedthrough capacitor assembly in which the EMI filter capacitor is placed inside of a cylindrical cavity with an optional thermo-setting polymer overfill.
Figure 28:
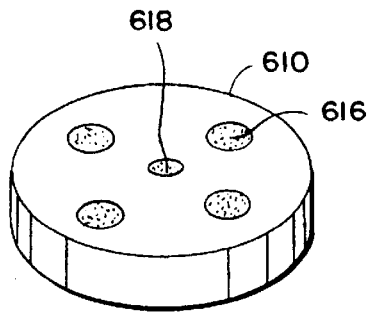
FIG. 28 is a perspective view of the quadpolar isolated ground capacitor of FIG. 27.
Figure 29:
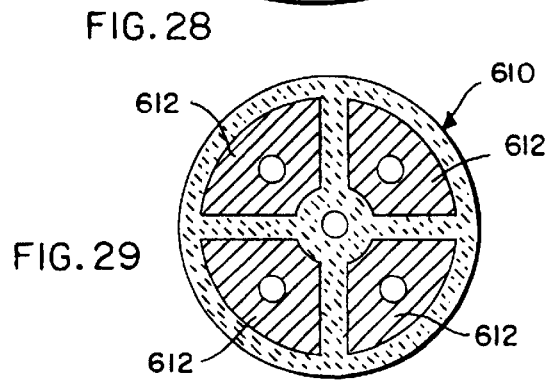
FIG. 29 is a top plan view of the active electrode plate sets of the quadpolar isolated ground feedthrough capacitor of FIG. 27.
Figure 27:
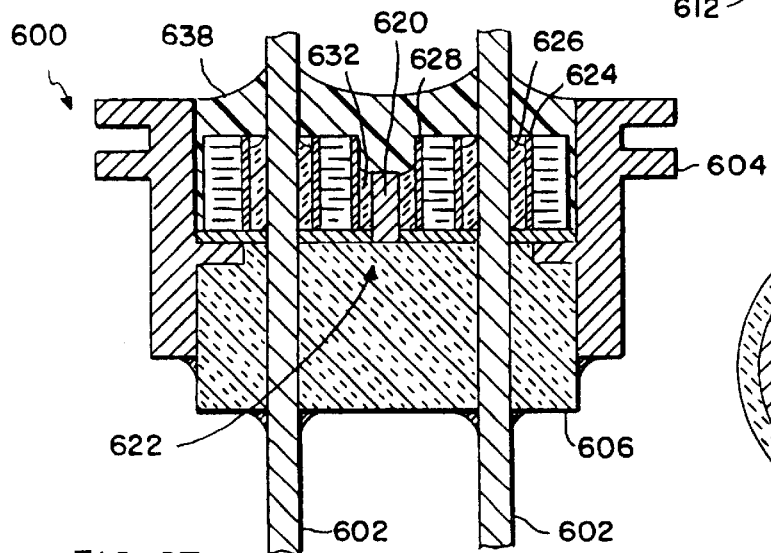
FIG. 27 is an enlarged, partially fragmented sectional view taken generally along the line 27—27 of FIG. 26.
Figure 30:
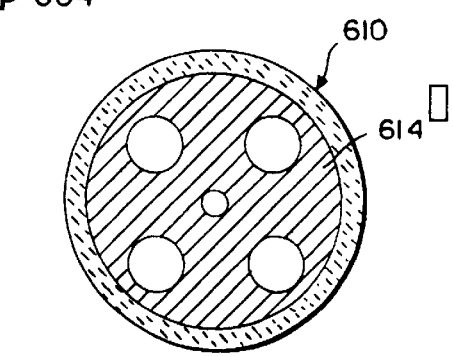
FIG. 30 is a top plan view of the common ground electrode plate set of the isolated ground capacitor of FIG. 27.
Figure 31:
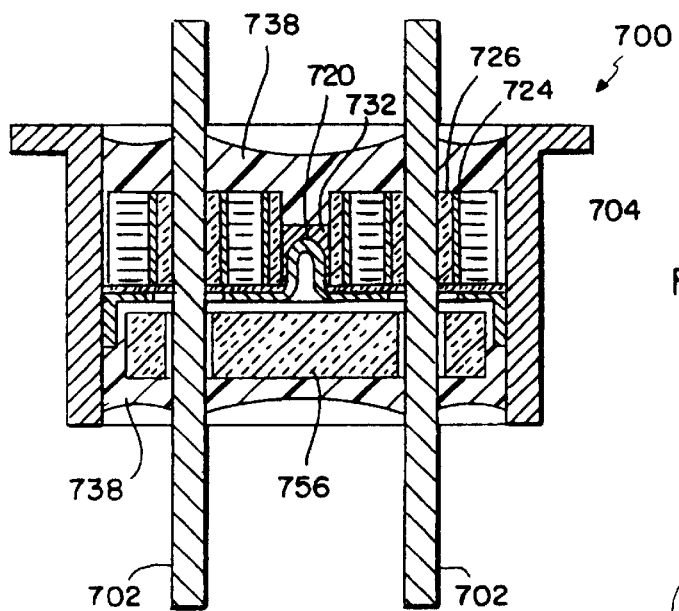
Figure 39:
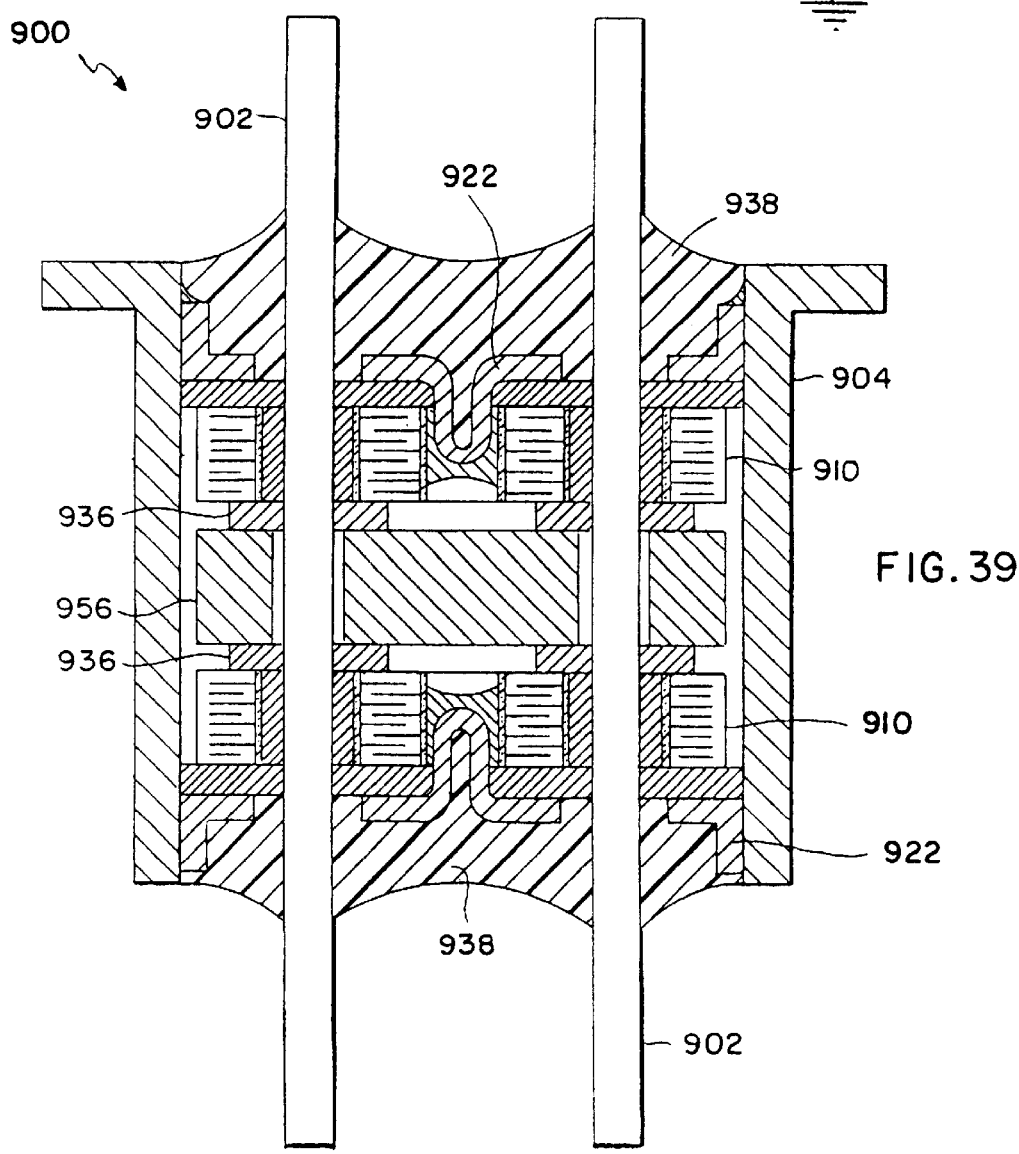
FIG. 39 is a cross sectional view of a soldered-in quadpolar isolated ground EMI filter that utilizes two of the ground plates described above in a Pi ($\pi$) circuit configuration.

As shown in the drawings for purposes of illustration, the present invention is concerned with novel internally ground feedthrough filter capacitor assemblies generally designated in FIGS. 1–5 by the reference number 100, in FIGS. 8 and 9 by the reference number 200, in FIGS. 14 and 15 by the reference number 300, in FIGS. 19–21 by the reference number 400, in FIGS. 22 and 23 by the reference number 500, in FIGS. 26 and 27 by the reference number 600, in FIG. 31 by the reference number 700, in FIG. 35 by the reference number 800, in FIG. 39 by the reference number 900, and in FIGS. 40 and 41 by the reference number 1000. In the following description, functionally equivalent elements of the various embodiments will share the same reference number in increments of 100.

Referring initially to FIGS. 1–5, the improved feedthrough filter capacitor assembly 100 comprises, generally, a plurality (five) of conductive terminal pins 102 and a conductive ferrule 104 through which the terminal pins pass in non-conductive relation. An insulator 106 supports each conductive terminal pin 102 relative to the conductive ferrule 104 in electrically insulated relation, and the assembly of the terminal pins and the conductive ferrule and insulator comprises a terminal pin subassembly 108. The feedthrough filter capacitor assembly 100 further includes a feedthrough filter capacitor 110 that has first and second sets of electrode plates 112 and 114. Passageways 116 are provided through the feedthrough filter capacitor 110 through which the terminal pins 102 extend in conductive relation with the first set of electrode plates 112. The feedthrough filter capacitor 110 further includes a second passageway 118 into which a ground lead 120 of an internal ground plate 122 extends. The ground lead 120 is conductively coupled to the second set of electrode plates 114. The ground lead 120 is either conductively coupled to the ground plate or plane 122 or is integrally formed therewith, and the ground plate, in turn, is conductively coupled to the conductive ferrule 104. Typically, the conductive ferrule is conductively mounted to a conductive substrate that may comprise, for example, the housing for an implantable medical device.

The invention as described herein eliminates the need for external conductive connections between the capacitor and a ground by connecting the internal ground plates to a ground pin, tubelet, or similar ground lead structure. This is a particularly convenient and cost effective approach for certain implantable medical devices that already employ a grounded terminal pin in order to use the titanium housing as a circuit reference point. Another convenient method to attach the internal ground plates is to use the hollow fill tubelet 50' (FIG. 23) of certain implantable devices which is used to evacuate and backfill with inert gasses. As there is no external electrical connection, the need for external capacitor metallization around the capacitor perimeter or outside diameter has also been eliminated. This not only reduces metallization firing or plating operations, but also eliminates the joining of materials which are not perfectly matched in thermal coefficient of expansion.

In other similar applications (non-medical), it is very typical to carry the ground or floating circuit ground connection through a connector (such connectors are widely used in space, military and telecommunications applications). Connection of the internally grounded capacitor electrode plates would be accomplished in a similar manner to that described above for medical implant devices.

In accordance with the present invention, the feedthrough filter capacitor 110 comprises a monolithic, ceramic, internally grounded bipolar feedthrough filter capacitor having two or more (for example six) passageways extending therethrough. The outer five passageways are configured to receive therethrough respective conductive terminal pins 102, and the internal diameter of the first passageways 116 are metallized (at 124) to form a conductive link between the first sets of electrode plates 112. A conductive polymide fill, solder, or the like 126 is placed within the first passageways 116 between the metallization 124 and the respective terminal pin 102 to electrically link the terminal pin with the respective first set of electrode plates 112. As is well understood in the art, the first sets of electrode plates 112 are typically silk-screened onto ceramic plates forming the feedthrough filter capacitor 110. These plates 112 are surrounded by an insulative ceramic material that, for purposes of the present invention, need not be metallized on its exterior surfaces.

Similarly, a second set of electrode plates 114 is provided within the feedthrough filter capacitor 110. The inner diameter of the central or second passageway 118 through the feedthrough filter capacitor 110 is also metallized (at 128) to conductively connect the second set of electrode plates 114, which comprise the ground plane of the feedthrough filter capacitor 110. The second passageway 118 is configured to receive therethrough the ground lead 120 which, in this particular embodiment, comprises a ground pin that is mechanically and electrically attached to a stamped titanium plate 130, such that the plate 130 and the ground lead 120 collectively form the ground plate or plane 122. Again, a conductive polymide, solder or other conductive fill 132 is placed within the second passageway 118 between the ground lead 120 and the metallization 128 to conductively couple the ground lead to the second set of electrode plates 114.

Internally grounding a ceramic feedthrough capacitor through a ground lead has heretofore not been considered because such construction increases the electrical impedance (particularly inductance) of the connection between the internal capacitor ground electrode plates and the conductive ferrule. This results in a reduction of the high frequency attenuation of the filter capacitor structure. However, with cost becoming an increasingly important issue, the internal grounding method becomes an attractive alternative. This tradeoff is further enhanced by the natural tendency body tissues have to absorb (attenuate) and reflect RF energy at higher frequencies. The tendency to increase the impedance can be minimized by symmetrical placement of the ground pin. However, nonsymmetrical arrangements still provide a high (and acceptable) degree of attenuation.

Another way of stating this is that the reduction of filter attenuation by the internal ground at high frequency tends to be offset by the natural tendency of the human body to absorb (or attenuate) high frequency RF energy. The efficacy of the internal ground was recently demonstrated by laboratory testing (in vitro) performed by the Federal Food and Drug Administration Center for Devices and Radiological health (FDA-CDRH). A fully functional implantable cardioverter defibrillator (ICD) was fitted with the asymmetrical internally grounded feedthrough capacitor assembly (worst case from an impedance standpoint) and then placed within a standardized saline tank to simulate body fluids. The instrumented ICD was immune to the EM fields produced by various model cellular phones. This is a result similar to previous testing which demonstrated that cardiac pacemakers fitted with EMI filters described by either the '551 or '095 patents were also immune to the EM fields produced by digital cellular phones (this previous testing also demonstrated that when these filters were removed, the cardiac pacemakers were susceptible to the EM fields with instances of complete inhibition of the pacemaker output). Inhibition of the pacemaker output pulse, is of course, a potentially life threatening situation for patients who depend upon the implanted device output pulse for each and every heartbeat.

In the feedthrough filter capacitor assembly 100 of FIGS. 1–5, the plate 130 and the lead 120 are fabricated as a subassembly (the ground plate 122) and is subsequently attached to the ferrule 104 by welding, brazing, conductive bonding or the like. The circumferential attachment of the ground plate or plane 122 to the ferrule 104 may be 360 degrees or performed in discontinuous arcs in order to provide unobstructed air paths for passage of helium between the ground plate, the insulator 106 and the terminal pins 102 during fine leak testing. In high production volumes, this approach significantly reduces the overall cost in that the ferrule 104 may be manufactured by highly efficient screw machines and the ground plane 122 may be manufactured by low cost metal stamping, chemical etch or similar methods. The ground lead or pin 120 can be co-machined as one piece or added by welding, brazing, conductive bonding or the like, to the plate 130 of the ground plane 122. The ground pin may extend well above the capacitor surface if needed for convenient connection of an internal circuit or substrate to the housing (ground). Alternatively, the pin may also extend through the insulator to the body fluid side for convenient attachment to an electrode lead. Welding may be done by many methods including laser, electron beam, projection, or resistance techniques. As shown in FIG. 5, the insulator 106 (typically alumina ceramic) is shown formed, pressed, or machined with five integral pedestals 134 which insert/locate into the aforementioned ground plate 122. This provides a flat mounting surface for a non-conductive polymide washer 136 and feedthrough capacitor 110 which will be free of voids or air pockets.

The washer 136 provides an insulative barrier between the isolated ground feedthrough capacitor and the mounting surface of the terminal. The barrier provides additional electrical isolation between the terminal pins and ground, and provides mechanical stability for environmental exposures such as vibration and mechanical shock. The insulating washer 136 may be constructed by punching laser cutting, or preforming a non-conductive polymide matrix to the proper shape and number of feedthrough holes using a material such as Abelbond 71-7. The insulating washer 136 may further be constructed of a non-conductive epoxy which has been formed into a B-staged preform.

Figures 1, 2:
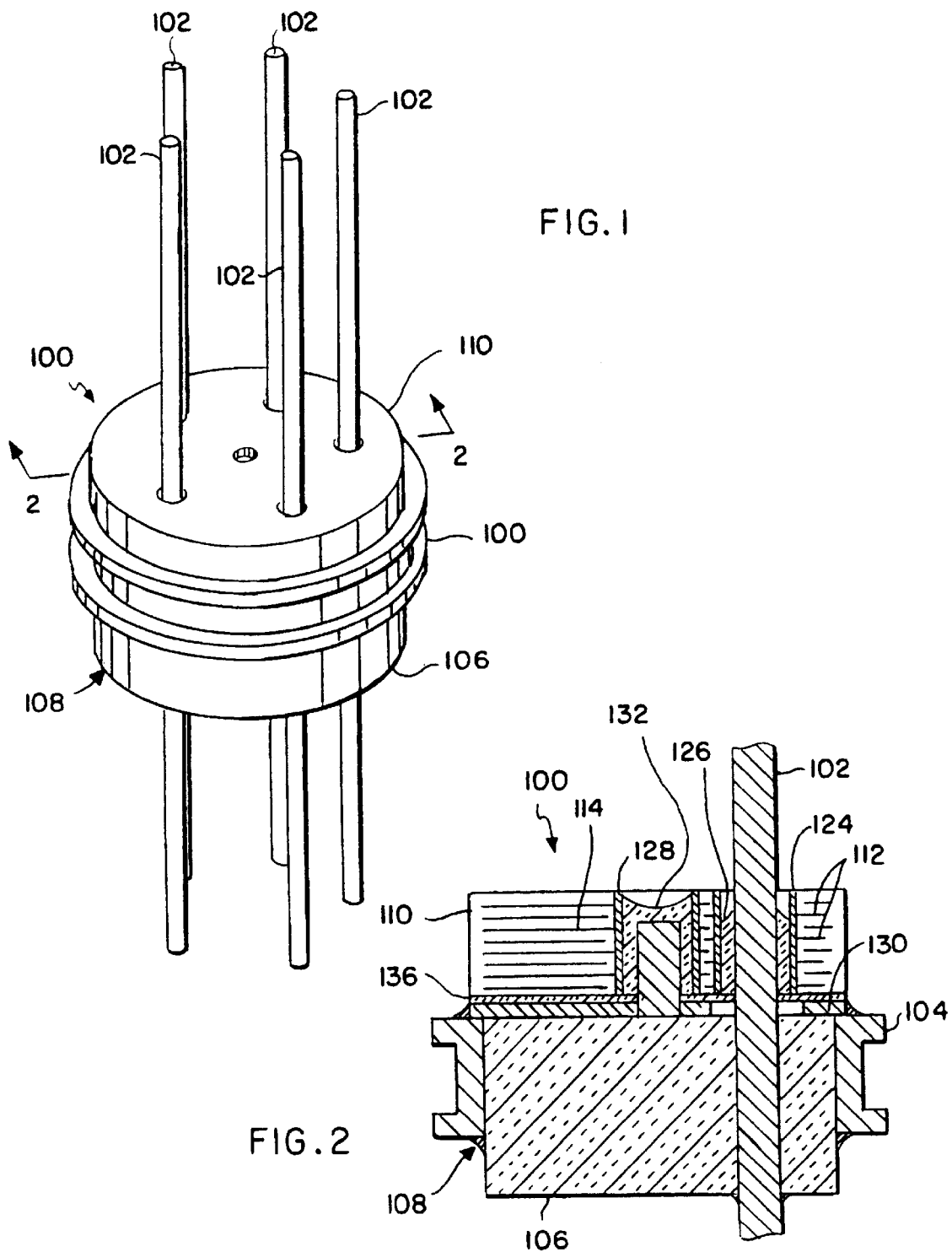
FIG. 1 is a perspective view of a monolithic ceramic, internally grounded, pentapolar feedthrough filter capacitor assembly embodying aspects of the present invention.
FIG. 2 is an enlarged, partially fragmented sectional view taken generally along the line 2—2 of FIG. 1.
Figure 3:
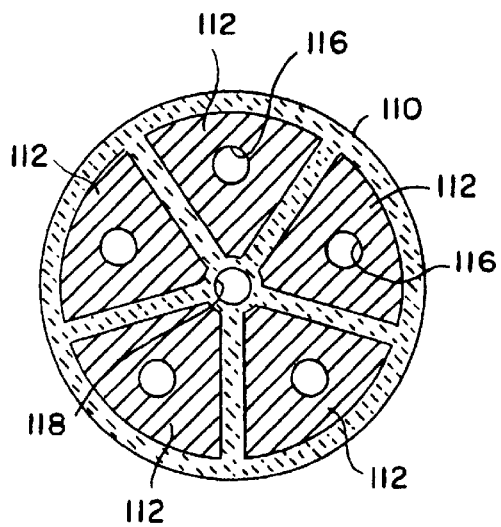
FIG. 3 is a sectional view taken through the capacitor of the assembly of FIGS. 1 and 2, illustrating the electrode plate lay-up pattern for the sets of five active electrodes.
Figure 4:
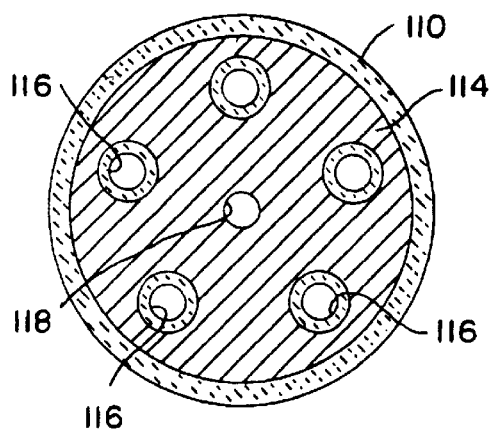
FIG. 4 is a sectional view similar to that shown in FIG. 3, illustrating the lay-up pattern for the set of ground electrode plates for the feedthrough capacitor of FIGS. 1 and 2.
Figure 5:
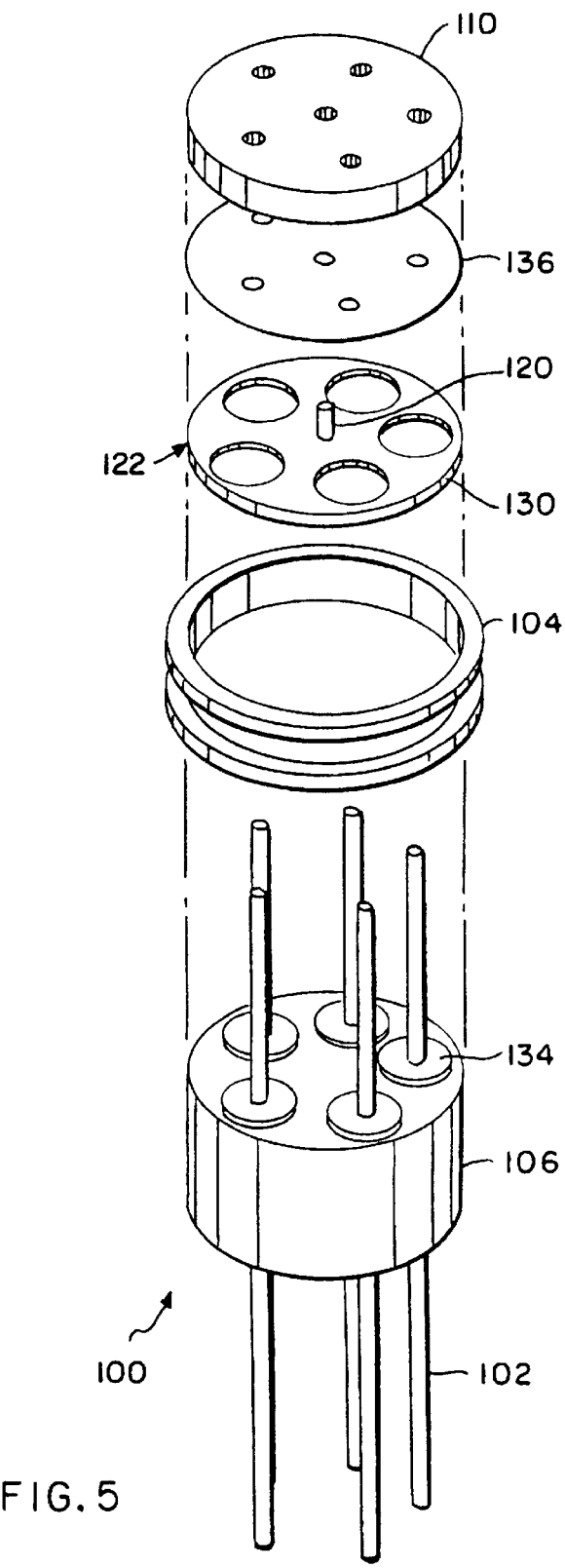
FIG. 5 is an exploded perspective view of the feedthrough filter capacitor assembly of FIGS. 1 and 2.
Figure 6:
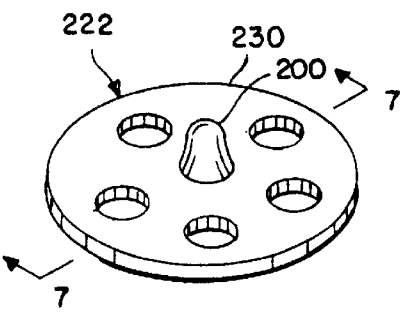
FIG. 6 is a top and side perspective view of an alternative ground plane that may be utilized in connection with the feedthrough filter capacitor assemblies of the present invention, wherein the ground pin is manufactured by metal forming or pressing as an integral part of the ground plane itself.
Figure 7:
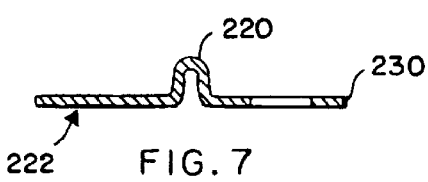
FIG. 7 is a sectional view taken generally along the line 7—7 of FIG. 6.

It will further be appreciated, with reference to FIGS. 3 and 4, that the electrode patterns of both the first and second sets of electrode plates 112 and 114 do not extend to the outer diameter of the feedthrough capacitor 110. This allows the outside surface of the feedthrough capacitor to be non-conductive (insulative).

In another embodiment shown in FIGS. 6–9, the feedthrough filter capacitor assembly 200 incorporates an alternate ground plane 222 wherein the ground lead 220 is manufactured by metal forming or pressing as an integral part of the plate 230 itself. This eliminates the need for a separate ground pin attachment by welding or brazing. The feedthrough filter capacitor assembly 200 is similar to the assembly 100 of FIGS. 1–5 in that there is shown a pentapolar hermetic terminal subassembly with the formed ground plane 222 having the integral terminal pin or ground lead 220 of FIGS. 6 and 7 conductively attached to the ferrule 204 by welding, brazing, bonding or the like. As is seen in FIG. 9, the ground lead 220 does not have to penetrate all the-way through the feedthrough capacitor 210. The exposed upper portion of the second conductive polymide or solder fill 228 can be optionally covered with an insulator 238 such as a non-conductive epoxy or polymide.

Figure 10:
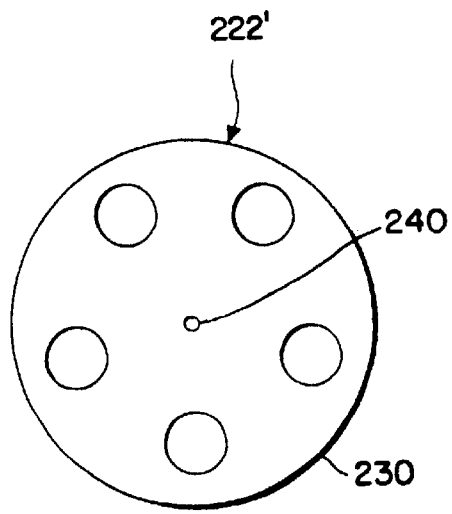
FIG. 10 is a top plan view of another form of ground plane created by chemical etching, punching, stamping or the like, such that a small center hole is formed for convenient locating of a forming tool or center punch.
Figure 11:
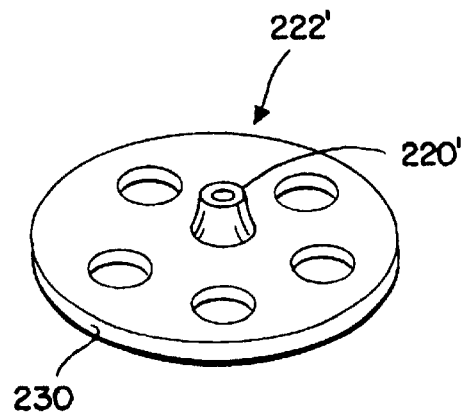
FIG. 11 is a perspective view of the ground plane of FIG. 10 after a punching operation to form a raised center protrusion which serves as a ground pin.
Figure 12:
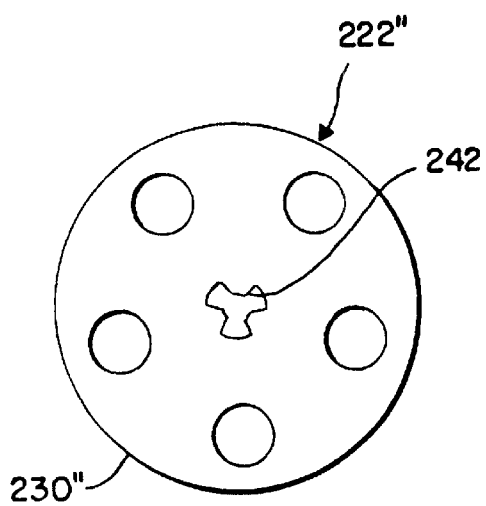
FIG. 12 is a top plan view of yet another form of ground plane which includes a cut-out pattern created at the location of a to-be-formed ground pin.
Figure 13:
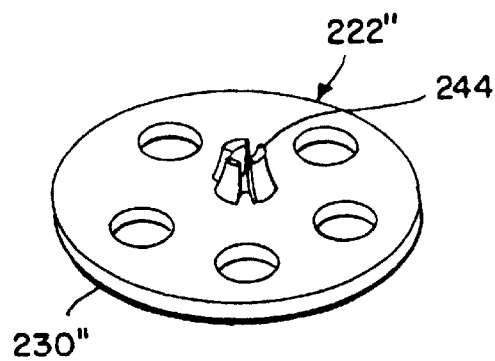
FIG. 13 is a top and side perspective view of the ground plane of FIG. 12 after a subsequent punching operation in order to fold up several tabs which collectively serve as the capacitor ground pin.

FIGS. 10 and 11 illustrate an alternative form of the ground plane or plate 222' which has been formed by chemical etch, punching, stamping or the like such that a small center hole 240 has been formed for convenient locating of a forming tool or center punch. As shown in FIG. 11, after a punching operation, a raised/formed center protrusion 220' is formed which is designed to fit inside of the second passageway 218 of the feedthrough capacitor 210. The raised/formed protrusion 220' thereby replaces the ground lead 220. Similarly, FIGS. 12 and 13 show another alternative form of the ground plane 222" which has been formed by chemical etch, punching, stamping or the like such that a cut-out pattern 242 is created at the location of the ground lead or pin 220. The cut-out pattern 242 may be used to locate a punch to facilitate the formation of bent-up tabs 244 which will form an integral "ground pin" 220" to be subsequently inserted into the second passageway 218 of the capacitor 210. The pattern shown is for illustrative purposes only, as many alternative patterns will be obvious to those skilled in the art.

FIGS. 14 and 15 illustrate another feedthrough filter capacitor assembly 300 similar to the assembly 100 of FIGS. 1–5. Here, however, the outer diameter of the insulator washer 336 has been notched out in five places to provide a hermetic leak path. In this embodiment, the pedestals 134 have also been eliminated from the insulator 306 to provide an air space 346 between the terminal pin subassembly 308 and the feedthrough capacitor 310 around each of the five terminal pins 302. This air space 346 acts in conjunction with the notched out areas of the insulator washer 336 so that an unobstructed leak path will be formed from each terminal pin. This is important during hermetic seal testing, such as a helium gas fine leak test, of the completed assembly so that the installation of the ceramic feedthrough capacitor 310 will not mask or hide a defective or leaky hermetic terminal pin 302.

FIGS. 16–18 simply illustrate a prior art pentapolar hermetic feedthrough filter capacitor assembly 1100. In this embodiment, common elements relative to the previously described embodiments will be designated by the same reference number preceded by 11*xx*. In this embodiment, the second set of electrode plates 1114 extend to the outer diameter of the feedthrough capacitor 1110. FIG. 16 illustrates an alumina insulator 1106, five terminal pins 1102, an exemplary feedthrough capacitor 1110 having externally applied sputtered metallizations 1128, five gold braze terminal pin preforms 1148, a titanium ferrule 1104 and a lower gold braze preform 1150. FIG. 17 is a perspective view of the prior art pentapolar hermetic seal terminal of FIG. 16 after vacuum brazing operations to reflow the gold braze preforms 1148 and 1150.

FIGS. 19–21 illustrate a pentapolar terminal with a sputtered-on ground plane and a counter-bored passageway to receive a ground pin 420 that is prepared for subsequent installation of an internally grounded feedthrough capacitor 410. More specifically, FIG. 19 is an exploded perspective assembly view of the pentapolar hermetic terminal similar to FIG. 16, but showing the ground plane 430 formed by sputter or similar metal deposition directly to the hermetic insulator 406 surface. Alternate metal deposition techniques include flame spray, electric arc, chemical plating and electroplating techniques, as well as silkscreening and firing on a conductive glass frit matrix, conductive electrode ink or other metallic thick film. This is a highly efficient process in that the ground plane 430 sputtering may be performed during the same operation as the sputtering that is required to form a metallized surface for subsequent formation of the gold brazed hermetic seals 448 and 450 between each terminal pin 402 and the insulator 406, and between the insulator 406 and the ferrule 404. FIGS. 20 and 21 illustrate the, novel pentapolar terminal with a sputtered ground plane 430 after vacuum brazing operations to reflow the gold braze preforms 448 and 450. The terminal pin subassembly 406 is then ready to accept installation of the internally grounded feedthrough capacitor 410 as illustrated. It will be noted that the ground lead 420 is provided is the form of a ground terminal pin that is placed within a shallow counter-bored or counter-sunk hole with metallization on the sides and bottom, and secured in place by its own conductive adhesive, solder connection or gold braze preform 452. Alternative embodiments will be obvious to those skilled in the art such as active brazing, direct sputtered metallization on hermetic seals formed by glass compression, glass fusion, single crystal ruby or sapphire or equivalent insulator instead of the alumina ceramic with gold braze that is illustrated.

FIGS. 22 and 23 illustrate a portion of a housing 554 of a neurostimulator or similar medical device wherein the hermetic seal to each terminal pin 502 is formed directly to the housing 554, thereby eliminating the need for a separate ferrule. The ground pin 520 may be attached by welding, brazing, bonding or the like. As shown, the ground pin 520 is preferably centrally located in relation to the feedthrough capacitor 510 in order to minimize ground plane electrode inductance and maximize EMI filter attenuation. Further, the ground pin 520 is shown as an optional hollow gas-fill tubelet for convenient vacuum evacuation of the implantable medical device and subsequent back-fill with an inert gas.

Figure 24:
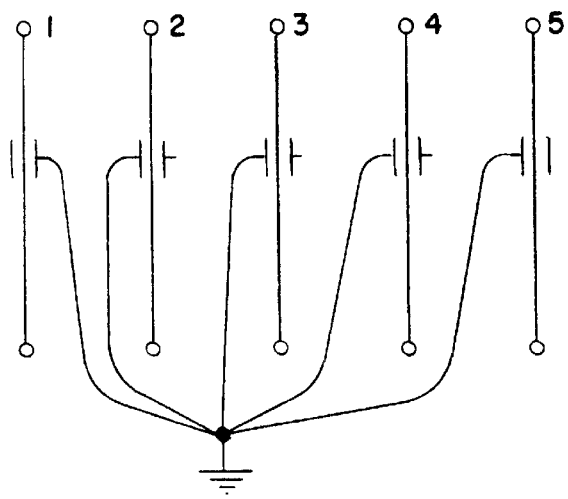
FIG. 24 is an electrical schematic for the illustrated pentapolar feedthrough capacitor assemblies.
Figure 25:
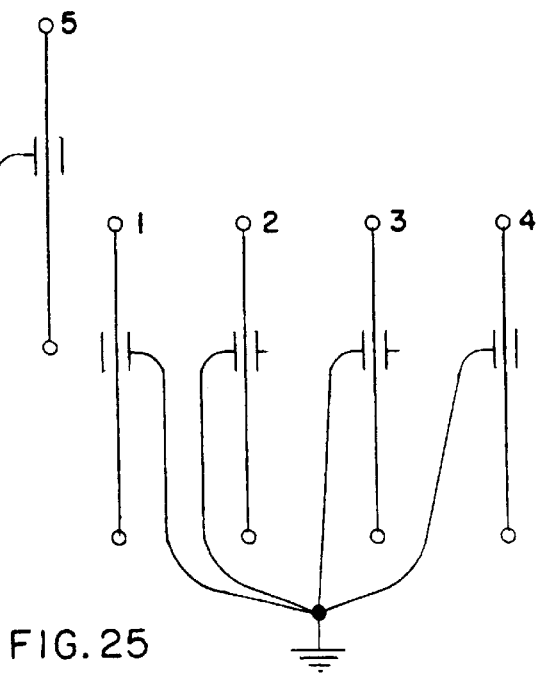
FIG. 25 is an electrical schematic for quadpolar feedthrough capacitor assemblies in accordance with the invention (as shown, for example, in FIGS. 22 and 23)

FIG. 24 is an electrical schematic of the pentapolar feedthrough capacitor assemblies shown in FIGS. 1–5, 8 and 9, 14 and 15 and 19–21. FIG. 25 is an electrical schematic of the quadpolar feedthrough capacitor assembly shown in FIGS. 22 and 23.

FIGS. 26–30 illustrate a quadpolar isolated ground EMI filter capacitor 610 which is placed inside of a cylindrical cavity. This assembly 600 may be installed so as to protrude from or into a titanium housing of a cardiac pacemaker or the like. The ground plane 622 with integral ground pin 620 may be fabricated as a machined/integral part of the ferrule 604 or as an adjunct thin plate as shown and previously described herein. A preferred mounting is to have the feedthrough filter capacitor assembly 600 protrude outside the housing of the implantable medical device. This design technique saves valuable space inside of the implantable medical device. Cardiac pacemakers, implantable defibrillators and other implantable medical devices are typically designed with an external polymer header or connector block to which the cardiac lead wires are connected. This connector block, which is often referred to by industry standards such as DF-1 or IS-1, typically has unutilized space into which the EMI quadpolar filter capacitor assembly 600 may protrude. In this embodiment the EMI filter case may also be used in place or in conjunction with the x-ray identification tag which is placed in the header block to identify the pacemaker manufacturer and model number. As shown in FIG. 27, an optional insulative polymer fill 638 may be provided over the capacitor 610 when installed within the ferrule 604.

Figure 32:
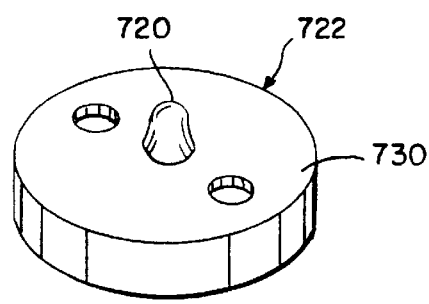
FIG. 32 is a top and side perspective view of the ground plane utilized in FIG. 31.
Figure 33:
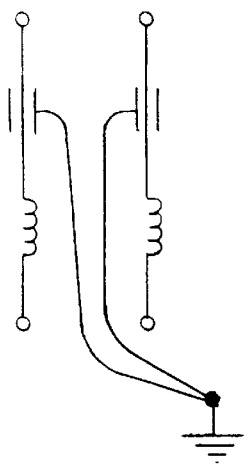
FIG. 33 is an electrical schematic representation of the bipolar EMI filter illustrated in FIG. 31.
Figure 34:
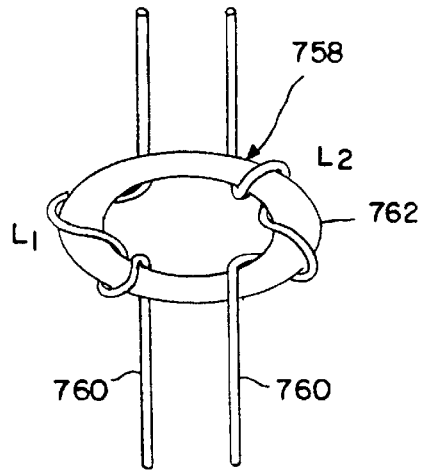
FIG. 34 is a perspective, schematic view of an optional bi-filar wound inductor that may be utilized in place of the ferrite inductor and leads shown in FIG. 31.

FIGS. 31–33 illustrate yet another feedthrough filter capacitor assembly 700 similar to the assembly 600, wherein a stamped or formed or etched ground plate 722 with a protruding ground lead or pin 720 is utilized. Typically, the ground plate 722 will be manufactured from a low cost metal (or metal-plated plastic) material for general industrial, military, space and other applications. In the preferred embodiment, the ground plate 722 is stamped from thin copper or brass sheet stock and then solder, gold, silver, tin coated or the like. FIG. 31 illustrated the ground plate 722 installed in a solder-in filter ferrule 704. Said ferrule 704 may be of any conductive material. In a preferred embodiment, the ferrule 704 is of cold roll steel and over-plated with gold, electro-tin, silver or the equivalent. The leads or terminal pins 702 may be copper or an other low cost highly conductive material. The filter assembly 700 may incorporate one or more ferrite inductors 756 in various EMI filter circuit configurations. The ground plate 722 is designed to fit to the inside diameter of the solder-in filter ferrule 704 and be electrically and mechanically attached by press-in fit, soldering, conductive polymer, resistance weld, other welding methods, brazing or other equivalent processes. FIG. 33 is a schematic drawing of the quadpolar EMI filter illustrated in FIG. 31, having the inductor 756. FIG. 34 is a perspective view of an optional bi-filar wound inductor 758 which may replace the ferrite inductor 756 and leads as shown in FIG. 32. To make the drawing easier to understand, only two of the four windings are shown. The windings 760 may be all wound in the same direction on a common core 762, or opposite pairs wound in opposite directions (bi-filar) to prevent core saturation for AC applications. Alternatively, two different inductors 758 may be used on opposite sides of the capacitor 710.

FIG. 35 illustrates a feedthrough filter capacitor assembly 800 having a ground plane washer 822 for an isolated ground feedthrough capacitor 810 which is fitted into the ferrule 804, wherein the ferrule has a convenient step or counter-bore 858 to seat/locate the ground plane washer 822. The ferrule 804 may be manufactured with or without a hermetic seal.

FIG. 36 is a side view of a quadpolar internal ground EMI filter showing optional mounting threads 60 and a hex head 62 for convenient screw-installation into a threaded hole or into a bulk head with a nut and lock washer. FIG. 37 is a side view of a quadpolar internal ground EMI filter similar to FIG. 36, showing an optional knurled surface 64 for installation by pressing into a mating hole into a bulk head or plate. These configurations may be applicable to any of the ferrules illustrated, if deemed necessary or desirable.

Figure 38:
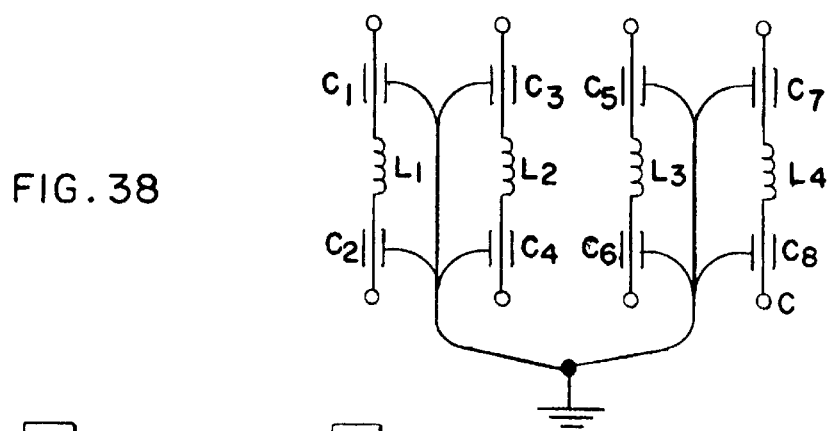
FIG. 38 is an electrical schematic representation for a quadpolar isolated ground EMI filter that utilizes two ground plates in a Pi ($\pi$) circuit configuration.

FIGS. 38 and 39 relate to a Pi ($\pi$) circuit EMI filter capacitor assembly 900. Here, two ground plates as illustrated in FIG. 32 are utilized with a respective pair of feedthrough capacitors 910 on opposite sides of an intermediate inductor 956. The ground plates 922 tend to protect the exposed outer surfaces of the capacitors 910 from epoxy fill stress.

FIGS. 40–43 illustrate a quadpolar feedthrough filter capacitor assembly 1000 that utilizes a pair of ground leads 1020 which are attached to a plate 1030, wherein the ground leads and the plate cooperatively form the ground plane 1022.

A significant advantage of the novel internally grounded feedthrough capacitor assemblies as described herein is that the mechanical (and electrical) connection to the outside diameter of the capacitor is eliminated. In addition to eliminating manufacturing operations and reducing cost, this has the added effect of greatly reducing the mechanical stresses coupled to the relatively brittle ceramic capacitor structure caused by the mismatch in the thermal coefficient of expansion of the ceramic capacitor and the terminal or substrate to which it is mounted. This is particularly important for medical implant devices where the combined filter capacitor and hermetic terminal see high terminal stresses due to the requirement to weld said structure to the housing of the medical implant device. Thus, the capacitor structure is allowed to mechanically "float" in relative isolation from the surrounding materials.

Another advantage of the internally grounded feedthrough capacitor assemblies as described herein, when installed in conjunction with a hermetic seal terminal, is that by elimination of the mechanical and electrical connection to the outside perimeter or outside diameter, the possibility of an adjunct or false hermetic seal is reduced or eliminated. In prior art (in particular the feedthrough capacitor described by the '551 patent), the electrical/mechanical connection to the capacitor outside diameter is accomplished with a conductive thermosetting material such as silver filled epoxy or polymide. This material can mask a leaking or defective hermetic terminal (a long term helium leak test of up to several hours may be able to detect the leak defect, but is in practice impractical and too costly). The elimination of this polymer material is therefore an important benefit.

Another benefit is that the penetration of the internal electrode plates to the external perimeter or outside diameter of the capacitor has been eliminated. This results in a more physically robust capacitor design with less tendency to delaminate along the knitline or internal electrode lamination layer. Accordingly, there will be less tendency for the capacitor to fracture, delaminate or otherwise structurally fail under thermal, mechanical or piezoelectric stresses. The only point of electrode penetration will be the inside diameter of the cylindrical holes for lead connection. This will tend to make the capacitor a more solid, monolithic structure which is more resistant to moisture or solvent penetration.

The construction methods illustrated are ideally suited for low cost commercial applications where exotic biocompatible materials are not required. The internal ground plate(s) acts to isolate the ceramic capacitor from the case which makes for a very rugged package which will withstand very high installation or operational temperatures. For example, with a gold plated ferrule and conductive polymide electrical connections to the lead, the device may be continuously rated to 300 degrees C. and 500 degrees C. intermittently. The package is also mechanically very rugged in that the brittle ceramic capacitor is isolated from the ferrule. Accordingly, this makes the capacitor much more resistant to damage during ferrule installation (into a mounting surface, can, housing or bulkhead) by soldering, pressing or screw-in torque.

Another common problem with EMI filters is due to mishandling by the customer during installation with pliers or other such gripping tools. Gripping the outside of a filter case can cause damage to the relatively brittle ceramic capacitor. However, with the construction methods illustrated, the capacitor is isolated from the case or ferrule which makes it much more resistant to damage by gripping tools.

Although several embodiments of the invention have been described in detail for purposes of illustration, various further modifications may be made without departing from the spirit and scope of the invention. Accordingly, the invention is not to be limited, except as by the appended claims.

We claim:

1. A feedthrough filter capacitor assembly, comprising:
   at least one conductive terminal pin;
   a feedthrough filter capacitor having first and second sets of electrode plates and a first passageway through which the terminal pin extends in conductive relation with the first set of electrode plates;
   a conductive ferrule through which the terminal pin passes in non-conductive relation;
   a conductive ground plane including a plate substantially spanning and supporting an adjacent face of the feedthrough filter capacitor, the ground plane having a grounded terminal pin which extends into a second passageway through the feedthrough filter capacitor in conductive relation with the second set of electrode plates, the plate being conductively coupled to the ferrule at an outer periphery of the plate in discontinuous arcs; and a washer for electrically insulating the feedthrough filter capacitor from the conductive ferrule except for the conductive relation between the grounded terminal pin and the second set of electrode plates.

2. The feedthrough filter capacitor assembly of claim 1, including an inductor through which the conductive terminal pin passes in non-conductive relation.

3. The feedthrough filter capacitor assembly of claim 2, wherein the inductor is a ferrite inductor.

4. The feedthrough filter capacitor assembly of claim 2, wherein the inductor is a wound inductor.

5. The feedthrough filter capacitor assembly of claim 1, including an insulator disposed within the ferrule, for mounting the conductive terminal pin for passage through the conductive ferrule with the conductive terminal pin and the ferrule in non-conductive relation.

6. The feedthrough filter capacitor assembly of claim 5, wherein the insulator includes a pedestal which extends through a locating aperture of the conductive ground plane.

7. The feedthrough filter capacitor assembly of claim 1, wherein an outer peripheral surface of the feedthrough filter capacitor is non-conductive.

8. The feedthrough filter capacitor assembly of claim 1, wherein the grounded terminal pin is formed with the plate.

9. The feedthrough filter capacitor assembly of claim 8, wherein the grounded terminal pin is formed in a punching operation.

10. The feedthrough filter capacitor assembly of claim 8, wherein the grounded terminal pin is formed in a stamping operation.

11. The feedthrough filter capacitor assembly of claim 8, wherein the grounded terminal pin includes bent-up tabs.

12. The feedthrough filter capacitor assembly of claim 1, wherein the washer includes a notch at its outer periphery to provide a hermetic leak path adjacent to the conductive terminal pin.

13. The feedthrough filter capacitor assembly of claim 1, wherein the feedthrough filter capacitor comprises a PI ($\pi$) circuit EMI filter capacitor assembly.

14. The feedthrough filter capacitor assembly of claim 1, wherein the ferrule is incorporated into a conductive housing for an electronic device.

15. The feedthrough filter capacitor assembly of claim 1, wherein the grounded terminal pin is mechanically and electrically attached to the plate.

16. A feedthrough filter capacitor assembly utilized in connection with a conductive substrate, comprising:
    at least one conductive terminal pin;
    means for mounting the terminal pin for passage through an opening formed in the conductive substrate with the terminal pin and the substrate in non-conductive relation;
    a feedthrough filter capacitor having first and second sets of electrode plates, a first passageway through which the terminal pin extends in conductive relation with the first set of electrode plates, and a second passageway;
    a conductive ground plane including a plate conductively coupled to the conductive substrate at an outer periphery of the plate and substantially spanning and supporting an adjacent face of the feedthrough filter capacitor, and a grounded terminal pin conductively coupled to the plate and extending into the second passageway in conductive relation with the second set of electrode plates, wherein the plate is attached to the terminal pin mounting means in discontinuous arcs; and
    a washer for electrically insulating the feedthrough filter capacitor from the conductive ground plane except for the conductive relation between the grounded terminal pin and the second set of electrode plates.

17. The assembly of claim 16, wherein the feedthrough filter capacitor is asymmetrical.

18. The assembly of claim 16, wherein the feedthrough filter capacitor is symmetrical about the grounded terminal pin.

19. The assembly of claim 18, wherein the feedthrough filter capacitor comprises a discoidal capacitor.

20. The assembly of claim 16, wherein the terminal pin mounting means includes means for hermetically sealing passage of the terminal pin through the substrate opening.

21. The assembly of claim 16, wherein the terminal pin mounting means comprises a conductive ferrule adapted for mounting onto the substrate in a position extending through the substrate opening, and insulator means for supporting the terminal pin from the ferrule in electrically insulated relation.

22. The assembly of claim 21, wherein the terminal pin, the ferrule and insulator means comprise a prefabricated terminal pin subassembly.

23. The assembly of claim 21, wherein the insulator includes a pedestal which extends through a locating aperture of the conductive ground plane.

24. The assembly of claim 16, including an inductor adjacent to the feedthrough filter capacitor through which the terminal pin extends, and wherein the feedthrough filter capacitor includes non-metallized exterior surfaces.

25. The assembly of claim 16, wherein the grounded terminal pin is mechanically and electrically attached to the plate.

26. The assembly of claim 16, wherein the grounded terminal pin is formed with the plate.

27. The assembly of claim 16, wherein the washer includes a notch at its outer periphery to provide a hermetic leak path adjacent to the conductive terminal pin.

28. A feedthrough filter capacitor assembly, comprising:

at least one conductive terminal pin;

a feedthrough filter capacitor having first and second sets of electrode plates and a first passageway through which the terminal pin extends in conductive relation with the first set of electrode plates;

a conductive ferrule through which the terminal pin passes in non-conductive relation;

an insulator disposed within the ferrule for mounting the conductive terminal pin for passage through the conductive ferrule;

a conductive ground plane comprising a conductive coating on the insulator which substantially spans and supports an adjacent face of the feedthrough filter capacitor, the ground plane having a grounded terminal pin which extends into a second passageway through the feedthrough filter capacitor in conductive relation with the second set of electrode plates, the conductive coating being conductively coupled to the ferrule at an outer periphery of the conductive coating; and a washer for electrically insulating the feedthrough filter capacitor from the conductive ferrule except for the conductive relation between the grounded terminal pin and the second set of electrode plates.

29. A feedthrough filter capacitor assembly, comprising:

at least one conductive terminal pin;

a feedthrough filter capacitor having first and second sets of electrode plates and a first passageway through which the terminal pin extends in conductive relation with the first set of electrode plates;

a conductive ferrule through which the terminal pin passes in non-conductive relation, the ferrule including a conductive ground plane substantially spanning and supporting an adjacent face of the feedthrough filter capacitor, the ground plane having an integral grounded terminal pin which extends into a second passageway through the feedthrough filter capacitor in conductive relation with the second set of electrode plates; and a washer for electrically insulating the feedthrough filter capacitor from the conductive ferrule except for the conductive relation between the grounded terminal pin and the second set of electrode plates;

wherein the ferrule is incorporated into a conductive housing for an electronic device; and wherein the grounded terminal pin comprises a hollow gas-fill tubelet.

30. A feedthrough filter capacitor assembly utilized in connection with a conductive substrate, comprising:

at least one conductive terminal pin;

means for mounting the terminal pin for passage through an opening formed in the conductive substrate with the terminal pin and the substrate in non-conductive relation;

a feedthrough filter capacitor having first and second sets of electrode plates, a first passageway through which the terminal pin extends in conductive relation with the first set of electrode plates, and a second passageway;

an insulator disposed within the terminal pin mounting means for mounting the conductive terminal pin for passage therethrough;

a conductive ground plane conductively coupled to the conductive substrate and comprising a conductive coating on the insulator which substantially spans and supports an adjacent face of the feedthrough filter capacitor, the ground plane having a grounded terminal pin extending into the second passageway in conductive relation with the second set of electrode plates, the conductive coating being conductively coupled to the terminal pin mounting means at an outer periphery of the conductive coating; and a washer for electrically insulating the feedthrough filter capacitor from the conductive ground plane except for the conductive relation between the grounded terminal pin and the second set of electrode plates.

31. A feedthrough filter capacitor assembly, comprising:

at least one conductive terminal pin;

a feedthrough filter capacitor having first and second sets of electrode plates and a first passageway through which the terminal pin extends in conductive relation with the first set of electrode plates;

a conductive ferrule through which the terminal pin passes in non-conductive relation;

a conductive ground plane including a plate that is a distinct component from the ferrule, substantially spanning and supporting an adjacent face of the feedthrough filter capacitor, the ground plane having a grounded terminal pin which extends into a second passageway through the feedthrough filter capacitor in conductive relation with the second set of electrode plates, the plate being conductively coupled to the ferrule at an outer periphery of the plate; and a washer for electrically insulating the feedthrough filter capacitor from the conductive ferrule except for the conductive relation between the grounded terminal pin and the second set of electrode plates.

32. The feedthrough filter capacitor assembly of claim 31, wherein the grounded terminal pin is mechanically and electrically attached to the plate.

33. The feedthrough filter capacitor assembly of claim 31, including an insulator disposed within the ferrule, for mounting the conductive terminal pin for passage through the conductive ferrule with the conductive terminal pin and the ferrule in non-conductive relation.

34. The feedthrough filter capacitor assembly of claim 33, wherein the insulator includes a pedestal which extends through a locating aperture of the conductive ground plane.

35. The feedthrough filter capacitor assembly of claim 31, wherein an outer peripheral surface of the feedthrough filter capacitor is non-conductive.

36. The feedthrough filter capacitor assembly of claim 31, wherein the grounded terminal pin is formed with the plate.

37. The feedthrough filter capacitor assembly of claim 31, wherein the washer includes a notch at its outer periphery to provide a hermetic leak path adjacent to the conductive terminal pin.

38. The feedthrough filter capacitor assembly of claim 31, wherein the ferrule is incorporated into a conductive housing for an electronic device.

39. The feedthrough filter capacitor assembly of claim 31, including an inductor through which the conductive terminal pin passes in non-conductive relation.

40. The feedthrough filter capacitor assembly of claim 39, wherein the inductor is a ferrite inductor.

41. The feedthrough filter capacitor assembly of claim 39, wherein the inductor is a wound inductor.

42. The feedthrough filter capacitor assembly of claim 31, wherein the feedthrough filter capacitor comprises a PI ($\pi$) circuit EMI filter capacitor assembly.

43. A feedthrough filter capacitor assembly utilized in connection with a conductive substrate, comprising:

at least one conductive terminal pin;

means for mounting the terminal pin for passage through an opening formed in the conductive substrate with the terminal pin and the substrate in non-conductive relation;

a feedthrough filter capacitor having first and second sets of electrode plates, a first passageway through which the terminal pin extends in conductive relation with the first set of electrode plates, and a second passageway;

a conductive ground plane that is a distinct component from the conductive substrate, the ground plane including a plate conductively coupled to the conductive substrate at an outer periphery of the plate and substantially spanning and supporting an adjacent face of the feedthrough filter capacitor, and a grounded terminal pin conductively coupled to the plate and extending into the second passageway in conductive relation with the second set of electrode plates; and a washer for electrically insulating the feedthrough filter capacitor from the conductive ground plane except for the conductive relation between the grounded terminal pin and the second set of electrode plates.

44. The assembly of claim 43, wherein the feedthrough filter capacitor is asymmetrical.

45. The assembly of claim 43, wherein the feedthrough filter capacitor is symmetrical about the grounded terminal pin.

46. The assembly of claim 45, wherein the feedthrough filter capacitor comprises a discoidal capacitor.

47. The assembly of claim 43, wherein the terminal pin mounting means includes means for hermetically sealing passage of the terminal pin through the substrate opening.

48. The assembly of claim 43, wherein the terminal pin mounting means comprises a conductive ferrule adapted for mounting onto the substrate in a position extending through the substrate opening, and insulator means for supporting the terminal pin from the ferrule in electrically insulated relation.

49. The assembly of claim 48, wherein the terminal pin, the ferrule and insulator means comprise a prefabricated terminal pin subassembly.

50. The assembly of claim 48, wherein the insulator includes a pedestal which extends through a locating aperture of the conductive ground plane.

51. The assembly of claim 43, wherein the grounded terminal pin is mechanically and electrically attached to the plate.

52. The assembly of claim 43, wherein the plate is attached to the terminal pin mounting means in discontinuous arcs.

53. The assembly of claim 43, wherein the grounded terminal pin is formed with the plate.

54. The assembly of claim 43, including an inductor adjacent to the feedthrough filter capacitor through which the terminal pin extends, and wherein the feedthrough filter capacitor includes non-metallized exterior surfaces.

55. The assembly of claim 43, wherein the washer includes a notch at its outer periphery to provide a hermetic leak path adjacent to the conductive terminal pin.

56. The assembly of claim 43, wherein the ground plane is formed by chemical etching.

* * * * *